US011819546B2

(12) United States Patent
Sutton

(10) Patent No.: US 11,819,546 B2
(45) Date of Patent: Nov. 21, 2023

(54) HELICOBACTER THERAPEUTIC

(71) Applicant: Murdoch Children's Research Institute, Parkville (AU)

(72) Inventor: Philip Sutton, Parkville (AU)

(73) Assignee: Murdoch Childrens Research Institute, Parkville (AU)

( * ) Notice: Subject to any disclaimer, the term of this patent is extended or adjusted under 35 U.S.C. 154(b) by 0 days.

(21) Appl. No.: 17/459,715

(22) Filed: Aug. 27, 2021

(65) Prior Publication Data

US 2022/0193216 A1   Jun. 23, 2022

Related U.S. Application Data

(63) Continuation of application No. 16/574,625, filed on Sep. 18, 2019, now abandoned, which is a continuation of application No. 15/321,933, filed as application No. PCT/AU2015/000380 on Jun. 30, 2015, now abandoned.

(30) Foreign Application Priority Data

Jun. 30, 2014 (AU) .............................. 2014902493

(51) Int. Cl.
*A61K 39/02* (2006.01)
*C07K 16/12* (2006.01)
*A61K 38/48* (2006.01)
*A61K 39/00* (2006.01)

(52) U.S. Cl.
CPC .......... *A61K 39/105* (2013.01); *A61K 38/482* (2013.01); *C07K 16/121* (2013.01); *A61K 2039/54* (2013.01); *A61K 2039/57* (2013.01); *C07K 2317/73* (2013.01); *C07K 2317/76* (2013.01)

(58) Field of Classification Search
CPC ................ A61K 39/105; A61K 38/482; A61K 2039/54; A61K 2039/57; C07K 16/121; C07K 2317/73; C07K 2317/76
See application file for complete search history.

(56) References Cited

U.S. PATENT DOCUMENTS

| | | | |
|---|---|---|---|
| 4,816,397 A | 3/1989 | Boss et al. | |
| 5,225,539 A | 7/1993 | Winter | |
| 5,693,761 A | 12/1997 | Queen et al. | |
| 5,939,400 A | 8/1999 | Steinman et al. | |
| 6,110,898 A | 8/2000 | Malone et al. | |

FOREIGN PATENT DOCUMENTS

| EP | 1092444 | 4/2001 |
|---|---|---|
| WO | WO-93/19183 | 9/1993 |
| WO | WO-95/20660 | 8/1995 |
| WO | WO-98/49314 | 11/1998 |
| WO | WO-99/34850 | 7/1999 |
| WO | WO-99/55871 | 11/1999 |
| WO | WO-01/13977 | 3/2001 |
| WO | WO-01/83531 | 11/2001 |
| WO | WO-01/90383 | 11/2001 |
| WO | WO-02/09746 | 2/2002 |
| WO | WO-02/34317 | 5/2002 |
| WO | WO-02/059148 | 8/2002 |
| WO | WO-2004/094467 | 11/2004 |
| WO | WO-2007/087576 | 8/2007 |
| WO | WO-2009/026615 | 3/2009 |
| WO | WO-2010/068413 | 6/2010 |

OTHER PUBLICATIONS

Bowie et al., "Deciphering the message in protein sequences: tolerance to amino acid substitutions," Science, 257, pp. 1306-1310 (1990).
Co, M.S. et al., "Humanized antibodies for antiviral therapy," PNAS USA, 88(7), pp. 2869-2873 (Apr. 1, 1991).
Database, GenBank, DAA34967.1, Aug. 9, 2011; Retrieved from the internet on Jul. 2, 2019, internet URL: https://www.ncbi.nlm.nih.gov/protein/DAA34967.1 (2 pages).
Database, GenBank, EJC07480; serine protease HtrA [Helicobacter pylon Hp P-26] BCT Jun. 28, 2012; Retrieved from the internet on Apr. 17, 2019, internet URL: https://www.ncbi.nlm.nih.gov/protein/ejc07480 (2 pages).
Database, GenBank, EJC09766; serine protease HtrA [Helicobacter pylon Hp P-26] BCT Jun. 28, 2012; Retrieved from the internet on Apr. 17, 2019, internet URL: https://www.ncbi.nlm.nih.gov/protein/ejc09766 (2 pages).
Database, GenBank, EJC10337; serine protease HtrA [Helicobacter pylon Hp P-26] BCT Jun. 28, 2012; Retrieved from the internet on Apr. 17, 2019, internet URL: https://www.ncbi.nlm.nih.gov/protein/ejc10337 (2 pages).
Database, GenBank, EJC13564; serine protease HtrA [Helicobacter pylon Hp P-26] BCT Jun. 28, 2012; Retrieved from the internet on Apr. 17, 2019, internet URL: https://www.ncbi.nlm.nih.gov/protein/ejc13564 (2 pages).
Database, GenBank, EJC53274; serine protease HtrA [Helicobacter pylon Hp P-26] BCT Jun. 28, 2012; Retrieved from the internet on Apr. 17, 2019, internet URL: https://www.ncbi.nlm.nih.gov/protein/ejc53274 (2 pages).
Extended European Search Report corresponding to EP 15814180.4 (PCT/AU2015/000380) dated Dec. 1, 2017 (8 pages).
Greenspan et al., "Defining epitopes: It's not as easy as it seems," Nature Biotechnology, 7, pp. 936-937 (1999).
Haas, Gaby et al., "Immunoproteomics of Helicobacter pylori infection and relation to gastric disease," Proteomics, 2, pp. 313-324 (2002; Received Jul. 20, 2001).

(Continued)

*Primary Examiner* — Robert A Zeman
(74) *Attorney, Agent, or Firm* — Mintz, Levin, Cohn Ferris, Glovsky and Popeo, P.C.

(57) ABSTRACT

The present invention relates to method of treating and/or preventing inflammation in a subject caused by bacteria that express HtrA. The present invention further relates to immunogenic compositions comprising an HtrA polypeptide or fragment thereof, as well as a therapeutic and/or prophylactic vaccine for treating or preventing disease.

4 Claims, 10 Drawing Sheets
Specification includes a Sequence Listing.

(56) References Cited

OTHER PUBLICATIONS

Hoy, Benjamin et al., "Distinct Roles of Secreted HtrA Proteases from Gram-negative Pathogens in Cleaving the Junctional Protein and Tumor Suppressor E-cadherin," The Journal of Biological Chemistry, 287(13), pp. 10115-10120 (Mar. 23, 2012).

Hoy, Benjamin et al., "Helicobacter pylori HtrA is a new secreted virulence factor that cleaves E-cadherin to disrupt intercellular adhesion," EMBO Reports, 11(10), pp. 798-804 (Sep. 3, 2010).

International Search Report corresponding to PCT/AU2015/000380 dated Oct. 1, 2015; 7 pages.

Jones, P.T. et al., "Replacing the complementarity-determining regions in a human antibody with those from a mouse," Nature, 321(6069), pp. 522-525 (May 29-Jun. 4).

Levitt, M. et al., "Molecular dynamics of native protein. I. Computer simulation of trajectories," J. Mol. Biol., 168(3), pp. 595-617 (Aug. 15, 1983).

Löwer, M. et al., "Prediction of extracellular proteases of the human pathogen Helicobacter pylori reveals proteolytic activity of the Hp1018/19 protein HtrA," PLoS One, 3(10), e3510 (2008).

Löwer, Martin et al., "Inhibitors of Helicobacter pylori Protease HtrA Found by 'Virtual Ligand' Screening Combat Bacterial Invasion of Epithelia," PLOS ONE, 6(3), 8 pages (Mar. 31, 2011).

Needleman, S.B. et al., "A general method applicable to the search for similarities in the amino acid sequence of two proteins," J. Mol. Biol. 48(3), pp. 443-453 (Mar. 1970).

Office Action dated Apr. 18, 2019 corresponding to Japanese Patent Application No. 2017-519730 (10 pages).

Office Action dated Feb. 2, 2019 corresponding to Russian Patent Application No. 2017100658 (5 pages).

Search Report dated Feb. 2, 2019 corresponding to Russian Patent Application No. 2017100658 (2 pages).

Sutton, P. et al., "Post-immunisation gastritis and Helicobacter infection in the mouse: a long term study," Gut, 49(4), pp. 467-473 (Oct. 2001).

Sutton, Phil, "Vaccine development for Helicobacter pylon," Jun. 23, 2016, XP055428405; Retrieved from the internet on Nov. 24, 2017, internet URL: http://www.who.int/immunization/research/meetings_workshops/9._Helicobacter_pylori_vaccine_2016_PDVAC_2016.pdf.

Written Opinion of the International Searching Authority corresponding to PCT/AU2015/000380 completed Oct. 1, 2015 (7 pages).

Yarilin, A. A., "Osnovy immunologii," M .: Meditsina, pp. 172-174 (1999).

HELICOBACTER THERAPEUTIC

RELATED APPLICATIONS

This application is a continuation of U.S. patent application Ser. No. 16/574,625, filed Sep. 18, 2019, which is a continuation of, U.S. patent application Ser. No. 15/321,933, filed Dec. 23, 2016, which is the U.S. National Stage under § 371 of International Application No. PCT/AU2015/000380, filed Jun. 30, 2015, which claims the benefit of AU Application No. 2014902493, filed Jun. 30, 2014, each of which are incorporated in their entirety herein for all purposes.

FIELD

The present invention relates to a method of treating and/or preventing inflammation in a subject. The present invention further relates to immunogenic compositions comprising a polypeptide or fragment thereof, as well as a therapeutic and/or prophylactic vaccine for treating or preventing disease.

BACKGROUND

*Helicobacter pylori* are gram negative bacteria that are major pathogens of the human stomach. Infection typically occurs during childhood, with transmission being most probably via the oral-oral route. Once established, virtually all infections are for life and it is estimated that half the World's population is infected with these bacteria.

*H. pylori* infection drives a chronic gastritis that, in some individuals, is the main aetiological factor in the development of a range of pathologies, including gastric ulcers, duodenal ulcers, gastric MALT lymphoma and gastric adenocarcinoma. Gastric adenocarcinoma remains the third leading cause of death worldwide due to malignancy, behind lung and liver cancer. It is fully accepted that the development of these *H. pylori*-associated diseases is a direct result of chronic gastritis and the more severe the inflammation the more likely it is for these pathologies to develop.

*H. pylori* infection is currently treated by combination antibiotic therapy. However, the increasing development of antibiotic resistance is a serious concern. Failure rate for the first treatment is 20% and for the second treatment is 25%, making an overall failure rate after 2 rounds of treatment of 5%. With increasing rates of resistance, this rate is predicted to increase in coming years.

Since its discovery, there has been a large effort to develop an effective vaccine aimed at protecting against *H. pylori* infection. These efforts have thus far been completely unsuccessful. The main problem preventing the development of an effective vaccine is the inability to reliably produce sterilising immunity. There are a multitude of vaccine approaches that will reduce *H. pylori* colonisation in animal models but none that will completely eradicate it. Vaccinations of mice, either prophylactically or therapeutically, typically results in a 1-2 log reduction in bacterial numbers, while clinical trials have shown no evidence of any efficacy to date.

Moreover, protective immunity in mice induced by prophylactic vaccination is commonly associated with an increase in the severity of gastritis (termed post-immunisation gastritis), although this has not been reported for therapeutic vaccination.

Accordingly, there remains a need for effective prophylactic and therapeutic treatments of inflammation and diseases caused by *H. pylori*.

SUMMARY

The present inventors found that vaccinating a subject with an HtrA polypeptide reduces or prevents the development of bacteria induced inflammation and disease despite persistence of the bacterial infection post vaccination.

Accordingly, a first aspect provides a method of treating or preventing bacteria induced inflammation in a subject, the method comprising administering to the subject a bacterial HtrA polypeptide or fragment thereof of at least 10 amino acids, and/or an antibody that binds bacterial HtrA.

In one embodiment of the first aspect, the method comprises administering an immunogenic composition comprising a bacterial HtrA polypeptide or fragment thereof of at least 10 amino acids.

A second aspect provides use of a bacterial HtrA polypeptide or a fragment thereof of at least 10 amino acids, and/or an antibody that binds bacterial HtrA in the treatment or prevention of bacteria induced inflammation in a subject.

A third aspect provides use of a bacterial HtrA polypeptide or a fragment thereof of at least 10 amino acids, and/or an antibody that binds bacterial HtrA, in the manufacture of a medicament for the treatment or prevention of bacteria induced inflammation in a subject.

In one embodiment of the first to third aspects, the inflammation is induced by an enteropathogenic bacterium and the HtrA polypeptide is an enteropathogenic bacterial HtrA polypeptide or fragment thereof of at least 10 amino acids. In one particular embodiment, the enteropathogenic bacterium is selected from *Helicobacter pylori, Escherichia coli, Shigella flexneri*, and *Campylobacter jejuni* and/or the enteropathogenic bacteria HtrA is selected from *Helicobacter pylori, Escherichia coli Shigella flexneri* and *Campylobacter jejuni* HtrA.

In another embodiment of the first to third aspects, the inflammation is induced by *Helicobacter pylori* and the HtrA polypeptide is a *Helicobacter pylori* HtrA polypeptide or fragment thereof of at least 10 amino acids.

In another embodiment of the first to fourth aspects, the HtrA polypeptide or fragment thereof of at least 10 amino acids comprises an amino acid sequence at least 95% identical to any one of SEQ ID NOs:1-6 or to a fragment thereof of at least 10 amino acids.

In another embodiment of the first to third aspects, the HtrA polypeptide or fragment thereof of at least 10 amino acids comprises an amino acid sequence at least 95% identical to any one of SEQ ID Nos:7-36.

In another embodiment of the first to third aspects, the bacteria induced inflammation is gastritis and/or duodenitis.

In yet another embodiment of the first to third aspects, the inflammation is atrophic gastritis.

A fourth aspect provides an immunogenic composition comprising a bacterial HtrA polypeptide or a fragment thereof of at least 10 amino acids, and/or an antibody that binds bacterial HtrA, for use in the treatment or prevention of bacteria induced inflammation in a subject.

In one embodiment of the fourth aspect, the immunogenic composition comprises a bacterial HtrA polypeptide or a fragment thereof of at least 10 amino acids.

In another embodiment of the fourth aspect, the bacterial HtrA polypeptide or fragment thereof of at least 10 amino acids is a *Helicobacter pylori* polypeptide or fragment of at least 10 amino acids thereof.

In another embodiment of the fourth aspect, the composition comprises an HtrA polypeptide comprising an amino acid sequence at least 95% identical to any one of SEQ ID NOs:1-6 or a fragment thereof of at least 10 amino acids.

In another embodiment of the fourth aspect, the HtrA polypeptide or fragment thereof of at least 10 amino acids comprises an amino acid sequence at least 95% identical to any one of SEQ ID Nos:7-36.

In another embodiment of the fourth aspect, the composition comprises a pharmaceutically acceptable excipient and/or adjuvant.

In yet another embodiment of the fourth aspect, the immunogenic composition is a vaccine. In one particular embodiment, the immunogenic composition is a therapeutic vaccine.

A fifth aspect provides a pharmaceutical composition comprising an antibody that binds to bacterial HtrA polypeptide. Preferably, the antibody binds specifically to HtrA.

In one embodiment, the antibody binds *Helicobacter pylori* HtrA polypeptide.

In another embodiment of the fifth aspect, the antibody is a monoclonal antibody, a chimeric antibody, a humanised antibody, a human antibody, Fab, F(ab')2, or an scFv.

A sixth aspect provides use of the immunogenic composition described herein, the pharmaceutical composition described herein, or an antibody that binds bacterial HtrA in the manufacture of a medicament for the treatment or prevention of bacteria induced inflammation.

In one embodiment of the sixth aspect, the bacteria induced inflammation is *Helicobacter pylori* induced inflammation.

In another embodiment of the sixth aspect, the bacteria induced inflammation is gastritis and/or duodenitis. In one particular embodiment, the inflammation is atrophic gastritis.

A seventh aspect provides a method of making an immunogenic composition, the method comprising mixing an HtrA polypeptide or fragment thereof of at least 10 amino acids with a pharmaceutically acceptable excipient and/or adjuvant.

In one embodiment of the seventh aspect, the method comprises isolating an HtrA polypeptide. In one particular embodiment, the HtrA polypeptide is a recombinant HtrA polypeptide.

In an embodiment of the seventh aspect, the immunogenic composition is a vaccine.

An eighth aspect provides a method of treating or preventing a disease caused by *Helicobacter pylori* infection in a subject, the method comprising administering to the subject an HtrA polypeptide or fragment thereof of at least 10 amino acids.

In one embodiment of the eighth aspect, the method comprises administering to the subject an immunogenic and/or pharmaceutical composition comprising an HtrA polypeptide or fragment thereof of at least 10 amino acids.

In one embodiment of the seventh or eighth aspect, the HtrA polypeptide or fragment thereof of at least 10 amino acids is a *Helicobacter pylori* HtrA polypeptide or fragment thereof of at least 10 amino acids.

In another embodiment of the seventh or eighth aspect, the HtrA polypeptide comprises an amino acid sequence at least 95% identical to any one of SEQ ID Nos:1-6 or a fragment thereof of at least 10 amino acids.

In another embodiment of the seventh or eighth aspects, the HtrA polypeptide or fragment thereof comprises an amino acid sequence at least 95% identical to any one of SEQ ID Nos:7-36.

In one embodiment of the eighth aspect, the immunogenic composition comprises a pharmaceutically acceptable excipient and/or adjuvant.

In another embodiment of the eighth aspect, the disease caused by *Helicobacter pylori* infection is inflammation, gastritis, gastric ulcer, duodenal ulcer, gastric cancer, and/or mucosa-associated-lymphoid-tissue (MALT) lymphoma.

In one embodiment of the first and eighth aspects, the method comprises administering an attenuated bacteria or virus comprising the HtrA polypeptide or fragment thereof of at least 10 amino acids to the subject.

In one embodiment of the third to seventh aspects, the composition or medicament comprises an attenuated bacteria or virus comprising the HtrA polypeptide or fragment thereof of at least 10 amino acids to the subject.

A ninth aspect provides an attenuated bacterium or virus comprising an HtrA polypeptide or fragment thereof of at least 10 amino acids.

In one embodiment, the HtrA polypeptide or fragment thereof of at least 10 amino acids is a *Helicobacter pylori* HtrA polypeptide or fragment thereof of at least 10 amino acids.

In another embodiment, the HtrA polypeptide comprises an amino acid sequence at least 95% identical to any one of SEQ ID Nos:1-6 or a fragment thereof of at least 10 amino acids.

In yet another embodiment, fragment thereof comprises an amino acid sequence at least 95% identical to any one of SEQ ID Nos:7-36.

A tenth aspect provides a DNA vaccine comprising a polynucleotide encoding a bacterial HtrA polypeptide or fragment thereof of at least 10 amino acids.

In one embodiment, the polynucleotide encodes an HtrA polypeptide or fragment of at least 10 amino acids comprising an amino acid sequence at least 95% identical to any one of SEQ ID NOs:1-36.

In another embodiment, upon administration of the DNA vaccine to a subject, the polypeptide is expressed and an immune response to the polypeptide is produced.

As will be apparent, preferred features and characteristics of one aspect of the invention are applicable to many other aspects of the invention.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

The invention is hereinafter described by way of the following non-limiting Examples and with reference to the accompanying figures.

KEY TO THE SEQUENCE LISTING

Figure 1:
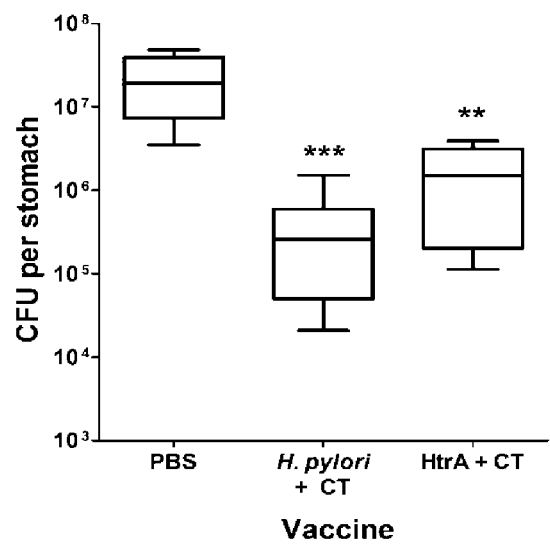
FIG. 1. Prophylactic vaccination with recombinant HtrA induces some protection against *H. pylori* challenge. Groups of mice (n=6) were vaccinated twice via the nasal route with killed *H. pylori* plus cholera toxin (CT) adjuvant (positive control) or HtrA plus CT. Negative controls were sham dosed with PBS (n=5). Four weeks after the second dose, all mice were challenged with live *H. pylori* strain SS1. Bacterial burdens in mouse stomachs were assessed four weeks later by colony forming assay. Vaccinations reduced bacterial colonisation compared to the negative control group ($p<0.01$, *$p<0.001$; ANOVA).

SEQ ID NO:1—Amino acid sequence of *H. pylori* HtrA polypeptide (Genbank accession: DAA34967).
SEQ ID NO:2—Amino acid sequence of *H. pylori* HtrA polypeptide (Genbank accession: EJC53274).
SEQ ID NO:3—Amino acid sequence of *H. pylori* HtrA polypeptide (Genbank accession: EJC13564).
SEQ ID NO:4—Amino acid sequence of *H. pylori* HtrA polypeptide (Genbank accession: EJC10337).
SEQ ID NO:5—Amino acid sequence of *H. pylori* HtrA polypeptide (Genbank accession: EJC09766).
SEQ ID NO:6—Amino acid sequence of *H. pylori* HtrA polypeptide (Genbank accession: EJC07480).
SEQ ID NOs:7-30—Amino acid sequences of *H. pylori* HtrA polypeptide fragments.
SEQ ID NO:31—Amino acid sequence of *H. pylori* HtrA polypeptide Trypsin domain.
SEQ ID NO:32-35—Amino acid sequences of *H. pylori* HtrA polypeptide PDZ 1 domains. SEQ ID NO:36—Amino acid sequence of *H. pylori* HtrA polypeptide PDZ 2 domain.
SEQ ID NOs:37-40—Oligonucleotide primers

DETAILED DESCRIPTION

General Techniques and Definitions

Unless specifically defined otherwise, all technical and scientific terms used herein shall be taken to have the same meaning as commonly understood by one of ordinary skill in the art (e.g., in immunology, microbiology and biochemistry).

Unless otherwise indicated, the molecular genetics, biochemistry, and immunological techniques utilized in the present invention are standard procedures, well known to those skilled in the art. Such techniques are described and explained throughout the literature in sources such as, J, Perbal, A Practical Guide to Molecular Cloning, John Wiley and Sons (1984), J. Sambrook and Russell., Molecular Cloning: A Laboratory Manual, 3$^{rd}$ edn, Cold Spring Harbour Laboratory Press (2001), R. Scopes, Protein Purification—Principals and Practice, 3$^{rd}$ edn, Springer (1994), T. A. Brown (editor), Essential Molecular Biology: A Practical Approach, Volumes 1 and 2, IRL Press (1991), D. M. Glover and B. D. Hames (editors), DNA Cloning: A Practical Approach, Volumes 1-4, IRL Press (1995 and 1996), and F. M. Ausubel et al. (editors), Current Protocols in Molecular Biology, Greene Pub. Associates and Wiley-Interscience (1988, including all updates until present), Ed Harlow and David Lane (editors) Antibodies: A Laboratory Manual, Cold Spring Harbour Laboratory, (1988), and J. E. Coligan et al. (editors) Current Protocols in Immunology, John Wiley & Sons (including all updates until present).

The terms "treating", "treat" or "treatment" as used herein include reference to administering an HtrA polypeptide or fragment thereof, an antibody that binds an HtrA polypeptide, or a composition or vaccine as described herein to reduce or eliminate at least one symptom of inflammation in a subject that is induced by a bacterium expressing HtrA.

The term "preventing" refers to protecting a subject that may be exposed or infected with bacteria expressing an HtrA polypeptide from developing at least one symptom of bacteria induced inflammation.

"Administering" as used herein is to be construed broadly and includes administering a composition or therapeutic agent as described herein to a subject or patient as well as providing the composition or therapeutic agent to a cell, such as, for example, by the provision of a prodrug to a patient.

The terms "specifically binds", "bind specifically", "specific binding" refer to the ability of an antibody to bind to a target molecular species in preference to binding to other molecular species with which the specific binding agent and target molecular species are admixed.

HtrA Serine Protease

HtrA is a serine protease and periplasmic chaperone in a number of enteropathogenic bacterial species including *Helicobacter pylori, Escherichia coli, Shigella flexneri*, and *Campylobacter jejuni*. Thus, the terms "HtrA polypeptide" or "HtrA polynucleotide" refer to a bacterial polypeptide or polynucleotide that has been assigned as or identified as, or is predicted to be, an HtrA on a database of gene or protein sequences such as Genbank or EMBL. In one embodiment, the HtrA polypeptide or polynucleotide is a sequence that belongs to the genome of any one of *Helicobacter pylori, Escherichia coli, Shigella jlexneri*, and *Campylobacter jejuni* on a sequence database. In a preferred embodiment, the HtrA polypeptide or polynucleotide is an *H. pylori* HtrA polypeptide or polynucleotide (i.e. a polypeptide or fragment thereof, or polynucleotide or fragment thereof, that is identified on a sequence database as being an HtrA sequence in the genome of *H. pylori*).

To date, HtrA is the only identified serine protease produced by *H. pylori*. It is a ~55 kDa protein that is both expressed on the bacterial surface and secreted. It is essential to bacterial survival, even for in vitro growth. Non-limiting examples of amino acid sequences of HtrA polypeptides include Genbank accession numbers DAA34967 (SEQ ID NO:1), EJC53274 (SEQ ID NO:2), EJC13564 (SEQ ID NO:3), EJC10337 (SEQ ID NO:4), EJC09766 (SEQ ID NO:5) and EJC07480 (SEQ ID NO:6).

The HtrA polypeptide used in the methods and compositions of the invention may be an isolated polypeptide that is purified directly from the bacteria from which it is derived using standard techniques in the art.

In one embodiment, the polypeptide is a recombinant polypeptide. The term "recombinant" in the context of a polypeptide includes reference to the polypeptide when produced by a cell in an altered amount or at an altered rate compared to its native state, as well as production of the polypeptide in a cell that does not naturally produce the polypeptide. The term "recombinant" also refers to the production of a polypeptide in a cell-free expression system.

The % identity of a polypeptide is determined by GAP (Needleman and Wunsch, (1970)) analysis (GCG program) with a gap creation penalty=5, and a gap extension penalty=0.3. The query sequence is at least 100 amino acids in length, and the GAP analysis aligns the two sequences over a region of at least 100 amino acids. In one example, the query sequence is at least 200 amino acids in length, and the GAP analysis aligns the two sequences over a region of at least 200 amino acids. In one example, the GAP analysis aligns two sequences over their entire length.

With regard to a defined polypeptide, it will be appreciated that % identity figures higher than those provided above will encompass preferred embodiments. Thus, where applicable, in light of the minimum % identity figures, it is preferred that the polypeptide comprises an amino acid sequence which is at least 80%, more preferably at least 85%, more preferably at least 90%, more preferably at least 91%, more preferably at least 92%, more preferably at least 93%, more preferably at least 94%, more preferably at least 95%, more preferably at least 96%, more preferably at least 97%, more preferably at least 98%, more preferably at least 99%, more preferably at least 99.1%, more preferably at least 99.2%, more preferably at least 99.3%, more preferably at least 99.4%, more preferably at least 99.5%, more preferably at least 99.6%, more preferably at least 99.7%, more preferably at least 99.8%, and even more preferably at least 99.9% identical to the relevant nominated SEQ ID NO.

Also included within the scope of the invention are immunogenic compositions and/or vaccines comprising a fragment of an HtrA polypeptide. In one embodiment, the fragment is an "immunogenic fragment" of an HtrA polypeptide.

In an embodiment, the fragment of the HtrA polypeptide is at least 8 amino acids in length, more preferably 9 amino acids in length, or more preferably at least 10 amino acids in length. Alternatively, the fragment is at least 11, 12, 13, 14, 15, 16, 17, 18, 19, 20, 30, 40, 50, 60, 70, 80, 90 or 100 or more amino acids in length. Non-limiting examples of fragments of HtrA polypeptides are provided as SEQ ID Nos:7-36. Thus, in one embodiment, the HtrA polypeptide administered to a subject is able to elicit an immune response to a polypeptide comprising an amino acid sequence selected from any one of SEQ ID Nos:1-36.

As would be understood by the person skilled in the art, an immunogenic composition, pharmaceutical composition and/or vaccine may comprise a domain of the HtrA polypeptide, such as, for example, a Trypsin domain, PDZ 1 domain or PDZ 2 domain. Example amino acid sequences of HtrA polypeptide domains are provide as SEQ ID NO:31 (Trypsin 2 domain), SEQ ID Nos:32-35 (PDZ 1 domain) and SEQ ID NO:36 (PDZ 2 domain).

Immunogenic Compositions and Vaccines

*Helicobacter pylori* has been strongly linked to the development of inflammation and gastric and duodenal ulcers, and it has been shown that eradication of *H. pylori* can prevent ulcers forming. Indeed patients presenting with ulcers should be tested for *H. pylori* and treated because eradication of *H. pylori* in patients with pre-existing ulcers cures ulcer disease and can prevent most recurrences. Gastric adenocarcinoma is the third leading cause of cancer death worldwide and there is strong evidence that *H. pylori* contributes to the development of gastric cancer. Although other factors such as a diet low in fruit/vegetables, smoking, age and a high salt intake also increase the risk of gastric cancer, *H. pylori* infection is most closely associated with stomach cancer. *H. pylori* infection can also lead to the development of a condition known as MALT Lymphoma a type of cancer of the stomach. Treatment and eradication of *H. pylori* infection can result in regression of this latter malignancy in up to 75% of cases.

Conventional treatment for *H. pylori* infection is a 7-day course of medication called Triple Therapy comprising two antibiotics, amoxicillin and clarithromycin, to kill the bacteria together with an acid suppressor to enhance the antibiotic activity. With the use of antibiotics to treat so many patients with various conditions it has become more difficult to treat *H. pylori* due to increasing occurrence of antibiotic resistant strains. As a result, up to 25% of patients fail the first line therapy.

In view of the failures of conventional therapy for *H. pylori* infection, the present inventors have found that vaccination of a subject with an HtrA polypeptide or a fragment thereof reduces or prevents the development of inflammation and/or disease caused by the bacterium. Without wishing to be bound by any particular theory, it is hypothesized that vaccination against HtrA induces neutralizing antibodies that block HtrA activity during infection. The lack of HtrA activity prevents the opening of the cell junctions and disruption of the epithelial barrier, thus preventing the transfer of bacterial components into the stomach tissue, protecting against induction of inflammation.

Accordingly, the present invention provides immunogenic compositions and vaccines for treating or preventing inflammation or a disease caused by infection of a subject with a bacterium expressing an HtrA polypeptide.

An "immunogenic composition" as used herein refers to a composition that comprises an HtrA polypeptide or a fragment thereof and that elicits an immune response against the HtrA polypeptide or a fragment thereof. The term "immunogenic composition" also includes reference to a "vaccine". The term "vaccine" covers any composition that induces an immune response that is at least partially protective against inflammation and/or disease caused by the targeted pathogen or which efficaciously protects against the pathogen and/or reduces colonization or infection by the pathogen. By inducing an "at least partially protective" immune response it is meant that a vaccine reduces or prevents bacteria induced inflammation, infection and/or colonization by a bacterium expressing an HtrA polypeptide or reduces at least one symptom caused by infection with a bacterium expressing an HtrA polypeptide. An immunogenic composition may select, activate or expand cells of the immune system including memory B and T cells to, for example, enable the production of antibodies or other immune mediators specific for the HtrA polypeptide or fragment thereof.

As understood in the art, the term "vaccination" refers to the process of administering a vaccine to a person, whereas the term "immunization" refers to the stimulation of the immune system to produce an at least partially protective immune response following vaccination.

The terms "antigen" and "antigenic" are well understood in the art and refer to the portion of a macromolecule which is specifically recognized by a component of the immune system, e.g., an antibody or a T-cell antigen receptor. The term "antigen" refers to a peptide, a polypeptide, or other macromolecule to which an immune response can be induced in a host. Thus the method of the invention may utilise an antigenic fragment of an HtrA polypeptide. Preferably, the antigenic fragment is capable of raising an immune response against a bacterial pathogen, for example a bacterium from the genus *Helicobacter* including, but not limited to, *Helicobacter pylori*. In one embodiment, the antigen is an epitope of the HtrA polypeptide. In one embodiment, the antigenic fragment is 6 amino acids in length, more preferably 7 amino acids in length, more preferably 8 amino acids in length, more preferably 9 amino acids in length, more preferably at least 10 amino acids in length. Alternatively the antigenic fragment is at least 20, 30, 40, 50, 60, 70, 80, 90, 100 or more amino acids in length. In an embodiment, the antigen when administered to a subject is able to elicit an immune response against the HtrA polypeptide.

The vaccines and/or immunogenic compositions of the invention may be administered by any suitable delivery route, such as intradermal, mucosal e.g. intranasal, oral, intramuscular or subcutaneous. Other delivery routes are well known in the art. Vaccine preparation is generally described in Vaccine Design ("The subunit and adjuvant approach" (eds Powell M. F. & Newman M. J.) (1995) Plenum Press, New York). In one embodiment, the immunogenic composition of the invention is administered by the intramuscular delivery route. Intramuscular administration may be to the thigh or the upper arm. Injection is typically via a needle (e.g. a hypodermic needle), but needle-free injection may alternatively be used. A typical intramuscular dose is 0.5 ml.

More recently, devices that are specifically designed to administer liquid agents into or across the skin have been described, for example the devices described in WO99/34850 and EP1092444, also the jet injection devices described for example in WO 01/13977. Alternative methods of intradermal administration of the vaccine preparations may include conventional syringes and needles, or devices designed for ballistic delivery of solid vaccines, or transdermal patches, or applied to the surface of the skin (transdermal or transcutaneous delivery).

When the vaccines or immunogenic compositions of the present invention are to be administered to the skin, or more specifically into the dermis, the vaccine is in a low liquid volume, particularly a volume of between about 0.05 ml and 0.2 ml. Another suitable administration route is the subcutaneous route. Any suitable device may be used for subcutaneous delivery, for example classical needle. In one aspect of the invention, a needle-free jet injector service is used, for example such as that published in WO 02/34317. In another aspect of the invention, the device is pre-filled with the liquid vaccine formulation.

In one embodiment, the vaccine is administered intranasally. Typically, the vaccine is administered locally to the nasopharyngeal area. Preferred devices for intranasal administration of the vaccines according to the invention are spray devices. Suitable commercially available nasal spray devices include Accuspray™ (Becton Dickinson).

The immunogenic composition and/or vaccine as described herein may be in the form of a therapeutic or prophylactic composition or vaccine. A prophylactic administration of an immunogenic composition or vaccine preferably protects the recipient from the development of inflammation and/or a disease, or delays the development of inflammation and/or disease, that would be caused by infection with bacteria comprising the HtrA polypeptide. A prophylactic composition or vaccine is administered to a patient who is not known to be infected with the bacteria, or is known to be free from infection with the bacteria, for example *H. pylori*, which expresses the HtrA polypeptide, or who has not yet been exposed to the bacteria. Alternatively, a therapeutic immunogenic composition and/or vaccine is administered to a subject known or expected to already be infected with the bacteria expressing the HtrA polypeptide, and who may already be exhibiting signs or symptoms of inflammation and/or disease caused by infection with the bacteria. The therapeutic composition and/or vaccine prevents or delays the progression of inflammation and/or disease caused by infection with the bacteria, or reduces the signs or symptoms of inflammation and/or disease caused by infection with the bacteria expressing the HtrA polypeptide.

Adjuvants are useful for improving the immune response and/or increasing the stability of vaccine preparations. Adjuvants are typically described as non-specific stimulators of the immune system, but also can be useful for targeting specific arms of the immune system. One or more compounds which have this activity may be added to the vaccine. Therefore, particular vaccines of the present invention further comprise an adjuvant. Suitable vaccine adjuvants include, but are not limited to, aluminium salts (aluminium phosphate or aluminium hydroxide), monophosphoryl lipid A (for example 3D-MPL), saponins (for example QS21), oil in water emulsions, blebs or outer membrane vesicle preparations from Gram negative bacterial strains (such as those taught by WO02/09746), lipid A or derivatives thereof, alkyl glucosamide phosphates or combinations of two or more of these adjuvants. In one embodiment the adjuvant is aluminium phosphate. In a further embodiment the adjuvant comprises 100-750, 150-600, 200-500, 250-450, 300-400, or around 350 µg aluminium as aluminium phosphate per human dose. In a further embodiment the adjuvant is aluminium hydroxide.

An "ISCOM-like adjuvant" is an adjuvant comprising an immune stimulating complex (ISCOM), which is comprised of a saponin, cholesterol, and a phospholipid, which together form a characteristic caged-like particle, having a unique spherical, caged-like structure that contributes to its function. This term includes both ISCOM adjuvants, which are produced with an antigen and comprise antigen within the ISCOM particle and ISCOM matrix adjuvants, which are hollow ISCOM-type adjuvants that are produced without antigen. In one embodiment, immunogenic composition and/or vaccine as described herein comprises an ISCOM matrix particle adjuvant, such as ISCOMATRIX™, which is manufactured without antigen (ISCOM™ and ISCOMATRIX™ are the registered trademarks of CSL Limited, Parkville, Australia).

In certain embodiments, the adjuvant is a cytokine. Certain compositions of the present invention comprise one or more cytokines, chemokines, or compounds that induce the production of cytokines and chemokines, or a polynucleotide encoding one or more cytokines, chemokines, or compounds that induce the production of cytokines and chemokines. Examples of cytokines include, but are not limited to granulocyte macrophage colony stimulating factor (GM-CSF), granulocyte colony stimulating factor (G-CSF), macrophage colony stimulating factor (M-CSF), colony stimulating factor (CSF), erythropoietin (EPO), interleukin 2 (IL-2), interleukin 3 (IL-3), interleukin 4 (IL-4), interleukin 5 (IL-5), interleukin 6 (IL-6), interleukin 7 (IL-7), interleukin 8 (IL-8), interleukin 9 (IL-9), interleukin 10 (IL-10), interleukin 11 (IL-11), interleukin 12 (IL-12), interleukin 13 (IL-13), interleukin 14 (IL-14), interleukin 15 (IL-15), interleukin 16 (IL-16), interleukin 17 (IL-17), interleukin 18 (IL-18), interferon alpha (IFNα), interferon beta (IFNβ), interferon gamma (IFNγ), interferon omega (IFNω), interferon tau (IFNτ), interferon gamma inducing factor I (IGIF), transforming growth factor beta (TGF-β), RANTES (regulated upon activation, normal T-cell expressed and presumably secreted), macrophage inflammatory proteins (e.g., MIP-1 alpha and MIP-1 beta), *Leishmania* elongation initiating factor (LEIF), and Flt-3 ligand.

In a further embodiment, the HtrA polypeptide or fragment thereof of at least 10 amino acids may be conjugated to a bacterial toxoid, such as a toxoid from diphtheria, tetanus, *E. coli* (e.g., a heat labile toxin), cholera, *H. pylori*, or other pathogen. Furthermore, the HtrA polypeptide or fragment thereof of at least 10 amino acids may be conjugated to a bacterial polysaccharide, such as the capsular polysaccharide from *Neisseria* sp., *Streptococcus pneumoniae* or *Haemophilus influenzae* type-b bacteria.

An excipient is an inactive substance formulated alongside the active ingredient ("API") of a medication, for the purpose of bulking-up formulations that contain potent active ingredients (thus often referred to as "bulking agents", "fillers", or "diluents"). Bulking up allows convenient and accurate dispensation of a drug substance when producing a dosage form. They also can serve various therapeutic-enhancing purposes, such as facilitating drug absorption or solubility, or other pharmacokinetic considerations. Excipients can also be useful in the manufacturing process, to aid in the handling of the active substance concerned such as by facilitating powder flowability or non-stick properties, in addition to aiding in vitro stability such as prevention of denaturation over the expected shelf life. As known in the art, the selection of appropriate excipients also depends upon the route of administration and the dosage form, as well as the active ingredient and other factors.

Other suitable adjuvants, which sometimes have been referred to as immune stimulants, include, but are not limited to: cytokines, growth factors, chemokines, supernatants from cell cultures of lymphocytes, monocytes, cells from lymphoid organs, cell preparations and/or extracts from plants, bacteria or parasites (*Staphylococcus aureus* or lipopolysaccharide preparations) or mitogens.

A further aspect of the invention is a method of making the vaccine and/or immunogenic composition of the invention comprising the steps of mixing an HtrA polypeptide or fragment thereof with a pharmaceutically acceptable excipient and/or adjuvant.

The HtrA polypeptide or fragment thereof of at least 10 amino acids can also be administered via liposome carriers, which serve to target the polypeptides to a particular tissue, such as lymphoid tissue, or to target selectively to infected cells, as well as to increase the half-life of the polypeptide composition. Liposomes include emulsions, foams, micelles, insoluble monolayers, liquid crystals, phospholipid dispersions, lamellar layers and the like. In these preparations, the polypeptide to be delivered is incorporated as part of a liposome, alone or in conjunction with a molecule which binds to a receptor prevalent among lymphoid cells (such as monoclonal antibodies which bind to the CD45 antigen or other costimulatory factor) or with other therapeutic or immunogenic compositions. Thus, liposomes either filled or decorated with a desired polypeptide can be directed to the site of lymphoid cells, where the liposomes then deliver the polypeptide compositions. Liposomes for use in accordance with the invention are formed from standard vesicle-forming lipids, which generally include neutral and negatively charged phospholipids and a sterol, such as cholesterol. The selection of lipids is generally guided by consideration of, e.g., liposome size, acid lability and stability of the liposomes in the blood stream. A variety of methods are available in the art for preparing liposomes. A liposome suspension containing an HtrA polypeptide or fragment thereof of at least 10 amino acids may be administered intravenously, locally, topically, etc. in a dose which varies according to, inter alia, the manner of administration, the polypeptide being delivered, and the stage of the disease being treated.

In one embodiment, the immunogenic composition and/or vaccine as described herein is administered together with, or in conjunction with, or as a combination with, a conventional therapy for treatment of bacterial infection. For example, the conventional therapy may be an organism-specific antibiotic. In the case of infection with *H. pylori*, the conventional therapy may be a combination of an antibiotic and an acid suppressor and/or stomach protector. Drugs that have been used to treat *H. pylori* infection include amoxicillin, clarithromycin, Rifabutin, Bismuth subsalicylate Furazolidone, Lactoferrin, Nitazoxanide and Levofloxacin. A combination that has been used to treat *H. pylori* infection includes Omeprazole (200 mg bd), Amoxycillin (1000 mg bd) and Clarithromycin (500 mg bd).

Attenuated Bacteria

In one embodiment, an HtrA polypeptide or fragment thereof of at least 10 amino acids is expressed by an attenuated bacterial (e.g., *Salmonella* sp.) or viral vaccine carrier (e.g., MVA). Methods of attenuating the virulence of bacterial pathogens are known in the art. Typically, mutations are introduced into a bacterial genome to prevent or reduce expression of toxins or other virulence genes to delete or inactivate the gene. In some instances, the function of the gene is knocked-out completely. This may be achieved by abolishing synthesis of any polypeptide at all from the gene or by making a mutation that results in synthesis of non-functional polypeptide. In order to abolish synthesis of polypeptide, either the entire gene or a portion, for example the 5'-end, may be deleted. A deletion or insertion within the coding sequence of a gene may be used to create a gene that synthesizes only non-functional polypeptide (e.g., polypeptide that contains only the N-terminal sequence of the wild-type protein). In the case of a toxin gene, the mutation may render the gene product non-toxic.

The present disclosure thus includes compositions comprising an attenuated bacterial or viral vaccine carrier which expresses an HtrA polypeptide or fragment thereof of at least 10 amino acids. The nucleic acid encoding the HtrA polypeptide may be in a vector or may be incorporated into the genome of the host carrier, for instance, by homologous recombination or genome editing (genome editing with engineered nucleases (GEEN). Examples of engineered nucleases suitable for genome editing include Transcription Activator-Like Effector Nucleases (TALENs), and the CRISPR/Cas system. In one embodiment of the invention, the vaccine composition comprises an attenuated *Salmonella* vaccine carrier comprising an attenuating mutation in a *Salmonella* Pathogenicity Island 2 region and, optionally, one or more additional attenuating mutations (for instance, a mutation in one or more of the aroA, aroC or sod genes) and a nucleic acid encoding an HtrA polypeptide or a fragment thereof of at least 10 amino acids. The attenuated live vaccine compositions of the present invention can further comprise, for instance, a pharmaceutically acceptable carrier, diluent and/or adjuvant.

Antibody Therapy

In addition to prophylactic and therapeutic vaccination, the present invention also includes antibody therapy for treatment of a patient having or suspected of having bacteria induced inflammation and/or disease. As used herein, the term "antibody therapy" includes reference to a treatment protocol or treatment regimen that includes the administration of an antibody to a subject. As would be understood in the art, the term "antibody therapy" encompasses both passive immunotherapy and passive immunoprophylaxis.

The term "antibody" as used herein refers to an immunoglobulin, immunoglobulin fragment, or immunoglobulin-like molecule capable of binding to a target, for example a bacterial HtrA polypeptide or fragment thereof. Thus, the term "antibody" encompasses not only intact polyclonal or monoclonal antibodies, but also bispecific antibodies, diabodies, triabodies, heteroconjugate antibodies, chimeric antibodies, humanized and human antibodies including intact molecules as well as fragments thereof, such as Fab, Fab', F(ab')2, Fv, and scFv which are capable of binding the HtrA polypeptide or fragment thereof.

As used herein, the term "monoclonal antibody" (mAb) refers to an antibody that is derived from a single copy or clone including, for example, any eukaryotic, prokaryotic, or phage clone, and not the method by which it is produced. mAbs used in the present invention preferably exist in a homogeneous or substantially homogeneous population. Complete mAbs contain two heavy chains and two light chains. Thus, fragments of such monoclonal antibodies include, for example, Fab fragments, Fab' fragments, F(ab)$_2$, single chain Fv fragments, and one-armed antibodies comprising a light chain and a heavy chain. Monoclonal antibodies and antigen-binding fragments thereof can be produced, for example, by recombinant technologies, phage display technologies, synthetic technologies, e.g., CDR-grafting, or combinations of such technologies, or other technologies known in the art.

Antibodies exhibiting desired functional properties, i.e., binding to an HtrA polypeptide or fragment thereof, can be generated by conventional methods. For example, mice can be immunized with an HtrA polypeptide or fragments thereof, the resulting antibodies can be recovered and purified, and determination of whether they possess the desired binding and functional properties can be assessed using known methods. Antigen-binding fragments can also be prepared by conventional methods. Methods for producing and purifying antibodies and antigen-binding fragments are well known in the art and can be found, for example, in Harlow and Lane (1988) Antibodies, A Laboratory Manual, Cold Spring Harbor Laboratory Press, Cold Spring Harbor, N.Y., chapters 5-8 and 15, ISBN 0-87969-314-2.

The phrase "humanized antibodies" refers to monoclonal antibodies and antigen binding fragments thereof that have framework regions that are substantially human or fully human surrounding CDRs derived from a non-human antibody. "Framework region" or "framework sequence" refers to any one of framework regions 1 to 4. Humanized antibodies and antigen binding fragments include molecules wherein any one or more of framework regions 1 to 4 is substantially or fully human, i.e., wherein any of the possible combinations of individual substantially or fully human framework regions 1 to 4, is present. For example, this includes molecules in which framework region 1 and framework region 2, framework region 1 and framework region 3, framework region 1, 2, and 3, etc., are substantially or fully human. Substantially human frameworks are those that have at least about 80% sequence identity to a known human germline framework sequence. Preferably, the substantially human frameworks have at least about 85%, at least about 90%, at least about 95%, or at least about 99% sequence identity to a known human germline framework sequence.

Fully human frameworks are those that are identical to a known human germline framework sequence. Human framework germline sequences can be obtained from ImMunoGeneTics (IMGT) via their website or from The Immunoglobulin FactsBook by Marie-Paule Lefranc and Gerard Lefranc, Academic Press, 2001, ISBN 012441351. For example, germline light chain frameworks can be selected from the group consisting of: AII, A17, A18, A19, A20, A27, A30, LI, L1I, L12, L2, L5, L15, L6, L8, O12, O2, and O8, and germline heavy chain framework regions can be selected from the group consisting of: VH2-5, VH2-26, VH2-70, VH3-20, VH3-72, VHI-46, VH3-9, VH3-66, VH3-74, VH4-31, VHI-18, VHI-69, VI-13-7, VH3-11, VH3-15, VH3-21, VH3-23, VH3-30, VH3-48, VH4-39, VH4-59, and VH5-5I.

Humanized antibodies can be generated using several different methods. In one approach, the parent antibody compound CDRs are grafted into a human framework that has a high sequence identity with the parent antibody compound framework. The sequence identity of the new framework will generally be at least about 80%, at least about 85%, at least about 90%, at least about 95%, or at least about 99% identical to the sequence of the corresponding framework in the parent antibody compound. In the case of frameworks having fewer than 100 amino acid residues, one, two, or three amino acid residues can be changed. This grafting may result in a reduction in binding affinity compared to that of the parent antibody. If this is the case, the framework can be back-mutated to the parent framework at certain positions based on specific criteria disclosed by Queen et al. (1991). Additional references describing methods useful in humanizing mouse antibodies include U.S. Pat. Nos. 4,816,397; 5,225,539; and 5,693,761; computer programs ABMOD and ENCAD as described in Levitt (1983); and the method of Winter and co-workers (Jones et al., 1986).

An antibody or antibody fragment, or immunogenic or pharmaceutical composition comprising the same, may be administered by parenteral routes (e.g., subcutaneous, intravenous, intraperitoneal, intramuscular, or transdermal). An antibody, or antigen-binding fragment thereof, of the present invention may be administered to a patient alone or in combination with a pharmaceutically acceptable carrier and/or excipient in single or multiple doses. Pharmaceutical compositions of the present invention can be prepared by methods well known in the art (e.g., Remington: The Science and Practice of Pharmacy, 19th ed. (1995), A. Gennaro et al., Mack Publishing Co.) and comprise an antibody, as disclosed herein, and one or more pharmaceutically acceptable carriers, diluents, or excipients.

In one embodiment there is provided a composition, e.g., a pharmaceutical composition, containing one or a combination of antibodies that bind an HtrA polypeptide, fragment or epitope thereof. The pharmaceutical compositions may be formulated with pharmaceutically acceptable carriers or diluents as well as any other known adjuvants and excipients in accordance with conventional techniques such as those disclosed in Remington: The Science and Practice of Pharmacy, 19th Edition, Gennaro, Ed., Mack Publishing Co., Easton, Pa., 1995.

Pharmaceutical compositions also can be administered in combination therapy, i.e., combined with other agents. For example, the combination therapy can include a composition with at least one anti-HtrA antibody and an anti-inflammatory agent. In one embodiment such anti-inflammatory agents include a steroidal drug or a NSAID (nonsteroidal anti-inflammatory drug). Examples of agents include, aspirin and other salicylates, Cox-2 inhibitors, such as rofecoxib (Vioxx) and celecoxib (Celebrex), NSAIDs such as ibuprofen (Motrin, Advil), fenoprofen (Nalfon), naproxen (Naprosyn), sulindac (Clinoril), diclofenac (Voltaren), piroxicam (Feldene), ketoprofen (Orudis), diflunisal (Dolobid), nabumetone (Relafen), etodolac (Lodine), oxaprozin (Daypro), and indomethacin (Indocin).

In one embodiment, an antibody that binds HtrA polypeptide is administered together with, or in conjunction with, or as a combination with, a conventional therapy for treatment of bacterial infection.

DNA Vaccines

DNA vaccination involves the direct in vivo introduction of DNA encoding an antigen into cells and/or tissues of a subject for expression of the antigen by the cells of the subject's tissue. Such vaccines are termed herein "DNA vaccines" or "nucleic acid-based vaccines." Examples of DNA vaccines are described in U.S. Pat. Nos. 5,939,400, 6,110,898, WO 95/20660 and WO 93/19183. The ability of directly injected DNA that encodes an antigen to elicit a protective immune response has been demonstrated in numerous experimental systems.

A factor known to affect the immune response elicited by DNA immunization is the method of DNA delivery, for example, parenteral routes can yield low rates of gene transfer and produce considerable variability of gene expression. High-velocity inoculation of plasmids, using a gene-gun, enhanced the immune responses of mice, presumably because of a greater efficiency of DNA transfection and more effective antigen presentation by dendritic cells. Vectors containing the nucleic acid-based vaccine of the invention may also be introduced into the desired host by other methods known in the art, e.g., transfection, electroporation, microinjection, transduction, cell fusion, DEAE dextran, calcium phosphate precipitation, lipofection (lysosome fusion), or a DNA vector transporter.

Treatment of Disease

The present inventors have determined that an HtrA polypeptide or fragment thereof of at least 10 amino acids, polynucleotide encoding an HtrA polypeptide or fragment thereof of at least 10 amino acids, an immunogenic composition, pharmaceutical composition, and/or vaccine as described herein can be administered to a subject, preferably a human subject, in order to treat or prevent bacteria induced inflammation and/or diseases resulting from infection with a bacterium that expresses the HtrA polypeptide. The present inventors have found that this treatment reduces or delays the development of signs or symptoms of inflammation and/or disease caused by infection with a bacterium expressing an HtrA polypeptide, despite the treatment not eradicating or preventing infection with the bacteria.

As would be understood in the art, the term "bacteria induced inflammation" refers to a biological response of tissues to harmful stimuli from bacteria, and includes both acute and chronic inflammation. The process of acute inflammation may be initiated by activation of innate immune cells already present in all tissues, mainly resident macrophages, dendritic cells, histiocytes, Kupffer cells and mastocytes. These cells present on their surfaces certain receptors named pattern recognition receptors (PRRs), which recognize molecules that are broadly shared by pathogens but distinguishable from host molecules, collectively referred to as pathogen-associated molecular patterns (PAMPs). At the onset of an infection may cells may undergo activation (one of their PRRs recognize a PAMP) and release inflammatory mediators responsible for the clinical signs of inflammation. Activation of this innate immune response then supports the activation of an acquired immune response, which particularly involves T-helper (Th) lymphocytes. *H. pylori* gastritis involves a mixed Th1 and Th17 type immune response marked by the pro-inflammatory cytokines IFNγ and IL-17, respectively. The severity of gastritis caused by these responses is regulated by production of immunosuppressive IL-10. Th2-type responses, for example, IL-13, also inhibit such responses. Vasodilation and its resulting increased blood flow causes the redness (rubor) and increased heat (calor). Increased permeability of the blood vessels results in an exudation (leakage) of plasma proteins and fluid into the tissue (edema), which manifests itself as swelling (tumor). Some of the released mediators such as bradykinin increase the sensitivity to pain (hyperalgesia, dolor). The mediator molecules also alter the blood vessels to permit the migration of leukocytes, mainly neutrophils, outside of the blood vessels (extravasation) into the tissue. The neutrophils migrate along a chemotactic gradient created by the local cells to reach the site of injury.

In addition to cell-derived mediators, several acellular biochemical cascade systems consisting of preformed plasma proteins act in parallel to initiate and propagate the inflammatory response. These include the complement system activated by bacteria. The exudative component involves the movement of plasma fluid, containing important proteins such as fibrin and immunoglobulins (antibodies), into inflamed tissue. This movement is achieved via the chemically induced dilation and increased permeability of blood vessels, which results in a net loss of blood plasma. The increased collection of fluid into the tissue causes it to swell (edema). This extravasated fluid is funneled by lymphatics to the regional lymph nodes, flushing cells exposed to H. pylori antigen along to start the recognition and attack phase of the adaptive immune system.

Acute inflammation is characterized by marked vascular changes, including vasodilation, increased permeability and increased blood flow, which are induced by the actions of various inflammatory mediators. Vasodilation occurs first at the arteriole level, progressing to the capillary level, and brings about a net increase in the amount of blood present, causing the redness and heat of inflammation. Increased permeability of the vessels results in the movement of plasma into the tissues, with resultant stasis due to the increase in the concentration of the cells within blood—a condition characterized by enlarged vessels packed with cells. Stasis allows leukocytes to marginate (move) along the endothelium, a process critical to their recruitment into the tissues.

Specific patterns of acute and chronic inflammation are seen during particular situations that arise in the body, such as when inflammation occurs on an epithelial surface, or pyogenic bacteria are involved.

1) Granulomatous inflammation: Characterized by the formation of granulomas, they are the result of a limited but diverse number of diseases, which include among others tuberculosis, leprosy, sarcoidosis, and syphilis.

2) Fibrinous inflammation: Inflammation resulting in a large increase in vascular permeability allows fibrin to pass through the blood vessels. If an appropriate procoagulative stimulus is present, such as cancer cells, a fibrinous exudate is deposited. This is commonly seen in serous cavities, where the conversion of fibrinous exudate into a scar can occur between serous membranes, limiting their function. The deposit sometimes forms a pseudomembrane sheet. During inflammation of the intestine (Pseudomembranous colitis), pseudomembranous tubes can be formed.

3) Purulent inflammation: Inflammation resulting in large amount of pus, which consists of neutrophils, dead cells, and fluid. Infection by pyogenic bacteria such as staphylococci is characteristic of this kind of inflammation. Large, localised collections of pus enclosed by surrounding tissues are called abscesses.

4) Serous inflammation: Characterized by the copious effusion of non-viscous serous fluid, commonly produced by mesothelial cells of serous membranes, but may be derived from blood plasma. Skin blisters exemplify this pattern of inflammation.

5) Ulcerative inflammation: Inflammation occurring near an epithelium can result in the necrotic loss of tissue from the surface, exposing lower layers. The subsequent excavation in the epithelium is known as an ulcer.

In one embodiment, the "bacteria induced" inflammation is gastritis (i.e., inflammation of the lining of the stomach) or duodenitis (i.e., inflammation of the duodenum). Erosive gastritis is gastric mucosal erosion caused by damage to mucosal defenses. Chronic gastritis refers to a wide range of problems of the gastric tissues.

In the case of gastritis induced by infection or colonization with Helicobacter pylori, acute infection may appear as an acute gastritis with abdominal pain (stomach ache) or nausea. Where this develops into chronic gastritis, the symptoms, if present, are often those of non-ulcer dyspepsia: stomach pains, nausea, bloating, belching, and sometimes vomiting or black stool. Individuals infected with H. pylori have a 10 to 20% lifetime risk of developing peptic ulcers and a 1 to 2% risk of acquiring stomach cancer. Inflammation of the pyloric antrum is more likely to lead to duodenal ulcers, while inflammation of the corpus (body of the stomach) is more likely to lead to gastric ulcers and gastric adenocarcinoma.

Mucous gland metaplasia, the reversible replacement of differentiated cells, occurs in the setting of severe damage of the gastric glands, which then waste away (atrophic gastritis) and are progressively replaced by mucous glands. Gastric ulcers may develop. Thus, in one embodiment, the bacteria induced inflammation is atrophic gastritis.

In one embodiment, there is provided a method of treating or preventing a disease caused by Helicobacter pylori infection in a subject. As known in the art, diseases caused by infection with H. pylori include inflammation, gastritis, duodenitis, atrophic gastritis, gastric ulcer, duodenal ulcer, gastric cancer, and/or mucosa-associated-lymphoid-tissue (MALT) lymphoma.

EXAMPLES

Example 1. Preparation of HtrA Antigen and Vaccinations

Recombinant HtrA (including mutant) was produced as described by Lower et al. (2008). The gene hp1018 was amplified from the genomic DNA of H. pylori strain 26695 by standard PCR using the Pfx DNA polymerase (Invitrogen, Karlsruhe, Germany). The following primers were used: hp1018 for: 5'-GGC TAT GGA TAA GGA TCA ACG C-3' (SEQ ID NO:37), hp1018rev: 5'-CCA CCG CCT TAA TAG AGT CCT T-3' (SEQ ID NO:38). The PCR product, having a calculated length of 333 bases, was submitted to a commercial provider (GENterprise, Mainz, Germany) for sequencing.

The construct Hp1018/19Dsp was amplified from genomic DNA of H. pylori strain 26695 using the primers 5'-aaggatccggcaatatccaaatccagagcatg-3' (SEQ ID NO:39) and 5'-aagaattcgacccaccccctatcatttcacc-3' (SEQ ID NO:40) with Pfx DNA polymerase in supplied buffer with 26 PCR Enhancer (Invitrogen). The amplified BamH1/EcoR1 flanked PCR product was then ligated into the pGEM-T Easy plasmid (Promega), subcloned into the pGEX-6P-1 plasmid DNA (GE Healthcare Life Sciences) and transformed in E. coli BL21. The construction of the protease-inactive Hp1018/19DspS205A protein, serine 205 was mutated to alanine using the QuikChangeH Lightning Site-Directed Mutagenesis Kit (Stratagene) according to the manufacturer's instructions. For heterologous overexpression and purification of GST-Hp1018/19Dsp, transformed E. coli was grown in 500 ml TB medium to an $OD_{550}$ of 0.6 and the expression was induced by the addition of 0.1 mM isopropylthiogalactosid (IPTG). The bacterial culture was pelleted at 4000 g for 30 minutes and lysed in 25 ml PBS by sonification. The lysate was cleared by centrifugation and the supernatant was incubated with glutathione sepharose (GE Healthcare Life Sciences) at 4° C. overnight. The fusion protein was either eluted with 10 mM reduced glutathione for 10 minutes at room temperature or cleaved with 180 U Prescission Protease for 16 h at 4° C. (GE Healthcare Life Sciences). Elution and cleavage products were analyzed by SDS PAGE and zymography.

Specific-pathogen free age-matched female C57BL/6 mice, bred within the Veterinary Science animal house, University of Melbourne, Parkville, were vaccinated twice with recombinant HtrA antigen (SEQ ID NO:1), three weeks apart via the nasal route. For nasal vaccination, the vaccine in a 30 µL volume was slowly applied to the external nares of the conscious mouse. Mice were immunized subcutaneously with 100 µg of formalin fixed *H. pylori*, 100 µg of alum, or 10 µg of HtrA plus 100 µg of alum.

Example 2. *H. pylori* Cultivation and Challenge of Mice

*H. pylori* strain SS1 was cultivated in brain heart infusion broth (BHI; Oxoid, Basingstoke, UK) containing 5% horse serum (JRH Biosciences, USA), 0.02% amphotericin B and Skirrow's Selective Supplements, under microaerophilic conditions at 37° C.

*H. pylori* lysate (HpL) was prepared by adding 0.1 mm glass beads (Daintree Scientific, St. Helens, TAS, Australia) to the bacteria and pulsing at 60 m/s using the FastPrep FP120 (Thermo Savant, Waltham, Mass., USA) in 30-second cycles with incubation on ice between cycles, until bacteria were lysed. Sterility was confirmed by culturing on horse blood agar plates. Protein levels were quantified using the BCA Protein Assay Kit (Pierce, Rockford, Ill., USA).

For formalin-fixation for vaccination, bacteria were suspended in 0.01 M formaldehyde in PBS and adjusted to an $OD_{600}$ of 1.5. After 2 hours gentle shaking at 37° C., the bacteria were shaken overnight at room temperature, washed 3 times in PBS and resuspended at $10^8$ bacteria/mL.

C57BL/6 mice used in these studies were age-matched females obtained from the Walter and Eliza Hall Institute, Melbourne. All animal experiments were approved by University of Melbourne Animal Ethics Committee.

Mice were infected intragastrically once with $10^7$ *H. pylori* strain SS1 suspended in 0.1 mL BHI. At completion of the experiment, mice were euthanized by $CO_2$ asphyxiation, and the stomachs opened along the inner curvature and divided into two halves. One half was used to quantify bacterial levels by colony-forming assay. The other half was fixed in neutral buffered formalin for histological assessment of gastritis.

Example 3. Colony Forming Assay

Four weeks after challenge, stomachs were opened along the inner curvature and divided into two halves. One half was placed in BHI broth and homogenized (GmbH Polytron® homogeniser, Kinematica, Switzerland). Ten-fold serial dilutions were prepared in BHI broth and aliquots spread over Glaxo selective supplement agar plates (Blood Agar Base No. 2, with 5% horse blood, 3.75 µg/mL Amphostat B, 12 µg/mL vancomycin, 0.4 µg/mL polymyxin B, 20 µg/mL bacitracin and 1.3 µg/mL nalidixic acid). After 5 days culture, colonies were counted and the number of colony forming units per stomach calculated.

Example 4. Gastric Pathology

Gastritis was assessed histologically as described previously (Sutton et al., 2001). The second halves of each stomach were fixed in 10% neutral buffered formalin, embedded in paraffin and 4 µm-thick sections cut. For assessment of gastritis, sections were stained with H&E and scored blinded under light microscopy. Inflammation was assessed in 2 separate tissue sections for each animal using 3 parameters. (1) cellular infiltration (migration of lymphocytes and neutrophils into the lamina propria) graded from 0 to 6, where 0, none; 1, mild multifocal; 2, mild widespread; 3, mild widespread and moderate multifocal; 4, moderate widespread; 5, moderate widespread and severe multifocal; and 6, severe widespread; (2) "mucus metaplasia" (large, pale, globular cells in the corpus) and (3) "atrophy" (loss of parietal and chief cells). Metaplasia and atrophy were graded from 0 to 3 (0, absent; 1, mild; 2, moderate; 3, severe).

Example 5. Gastric Cytokines

Cell debris was removed from stomach homogenates by centrifugation and protein concentrations in the supernatant quantified using a BCA protein assay kit (Pierce, Rockford, Ill., USA) prior to ELISA. Cytokine concentrations were determined by coating 96-well Maxisorp plates (Nunc, Roskilde, Denmark) with purified anti-mouse IL-13 (50 ng/well; eBioscience, San Diego, Calif., USA), IL-10 (100 ng/well; BD Biosciences, San Jose, Calif., USA), IFNγ (100 ng/well; BD Biosciences) or IL-17A (50 ng/well; eBioscience) overnight in bicarbonate coating buffer, pH 9.6. Plates were blocked with 1% BSA (Sigma) in PBS (blocker) for one hour prior to addition of samples in duplicate for three hours at room temperature or 4° C. overnight. Captured cytokines were then labelled with biotinylated anti-mouse IL-13 (25 ng/well; eBioscience), IL-10 (50 ng/well; BD Bio-sciences), IFNγ (50 ng/well; BD Biosciences) or IL-17A (25 ng/well; eBioscience) in blocker for one hour prior to the addition of 50 µL horseradish peroxidase conjugated streptavidin (Pierce) 1/5000 in blocker for 30 min. Colour was developed with 100 µL of TMB solution prepared as 0.1% of 10 mg/mL TMB (Sigma) in DMSO and 0.006% hydrogen peroxide in phosphate-citrate buffer, pH 5.0, and the reaction stopped with an equal volume of 2 M sulphuric acid prior to reading absorbance at 450 nm. Sample concentration was determined against a standard curve of recombinant IL-10, IFNγ (BD Biosciences), IL-13 and IL-17A (eBioscience).

Example 6. HtrA Serum Inhibition Assay

The EnzChek® peptidase/protease assay kit (E33758) was used to measure the ability of sera from the above vaccinated mice to block proteolytic activity of HtrA. Sera from vaccinated/infected mice (collected four weeks after challenge) were diluted 1:5 and mixed with either HtrA or PBS (control) using component B (digestion buffer) of the peptidase kit for 30 mins. The proteolytic activity of HtrA was then assessed by measuring cleavage of substrate following incubation for 60 min (as per kit recommendations). Absorbance was read at 502/528 nm using a TECAN Infinite M200Pro reader and data analysed using Magellan 7.1 SPI software.

Example 7. Quantification of Antibody Response to Infection

Sera were collected by cardiac puncture. Intestinal mucus scrapings were collected from the lower 10 cm of the longitudinally opened small intestine using a scalpel blade, weighed, then mixed with an equal volume of PBS containing complete mini-EDTA-free proteinase inhibitor cocktail (Roche Diagnostics, Mannheim, Germany). Anti-*Helicobacter* antibody levels were determined by direct ELISA. Maxisorp immunoplates (Nunc, Denmark) were coated overnight with 50 µg/well of *H. pylori* lysate in bicarbonate buffer pH9.6. Plates were blocked for 1 hour at RT. Samples were serially diluted 1/10 in blocker and 50 µL added to duplicate wells, before incubation at RT for 1 hour. Captured antibodies were labelled with horseradish peroxidase conjugated goat-anti-mouse IgG (4 ng/well; Pierce), goat-anti-mouse IgG1 (8 ng/well, Southern Biotech, Birmingham, Ala., USA) or IgA (10 ng/well, Southern Biotech) in blocker for 1 hour at RT. Colour was developed and read as above and end point titres calculated.

Example 8. Western Blotting

*H. pylori* lysate (20 µg/lane) was separated on 8% SDS-PAGE gels then transferred to nitrocellulose membranes (Amersham Biosciences). Membranes were blocked with 5% skim milk and probed with intestinal scrapings diluted 1/1,000. Bound primary antibodies were detected with horseradish peroxidase-conjugated anti-mouse antibodies (Dako). Labelled proteins were visualised by incubating the membrane in ECL Prime reagent (Amersham Biosciences) and using an ImageQuant LAS 4000 (GE Healthcare). All gels were exposed for 10 seconds.

Example 9. Statistics

Statistical analyses were performed using the Statistical Package for the Social Sciences software, version 21.0.

Example 10. Results

Prophylactic Vaccination with HtrA Induces Minimal Protection

Groups of mice were vaccinated twice via the nasal route with killed *H. pylori* plus cholera toxin (CT) adjuvant (positive control) or HtrA plus CT. Negative controls were sham dosed with PBS. Four weeks after the last dose, all mice were challenged with live *H. pylori* strain SS1. Bacterial burdens in mouse stomachs were assessed four weeks later by colony forming assay. Vaccinations reduced bacterial colonisation compared to the negative control group (FIG. 1; p<0.01, *p<0.0001; ANOVA).

Post Immunisation Gastritis

Figure 2:
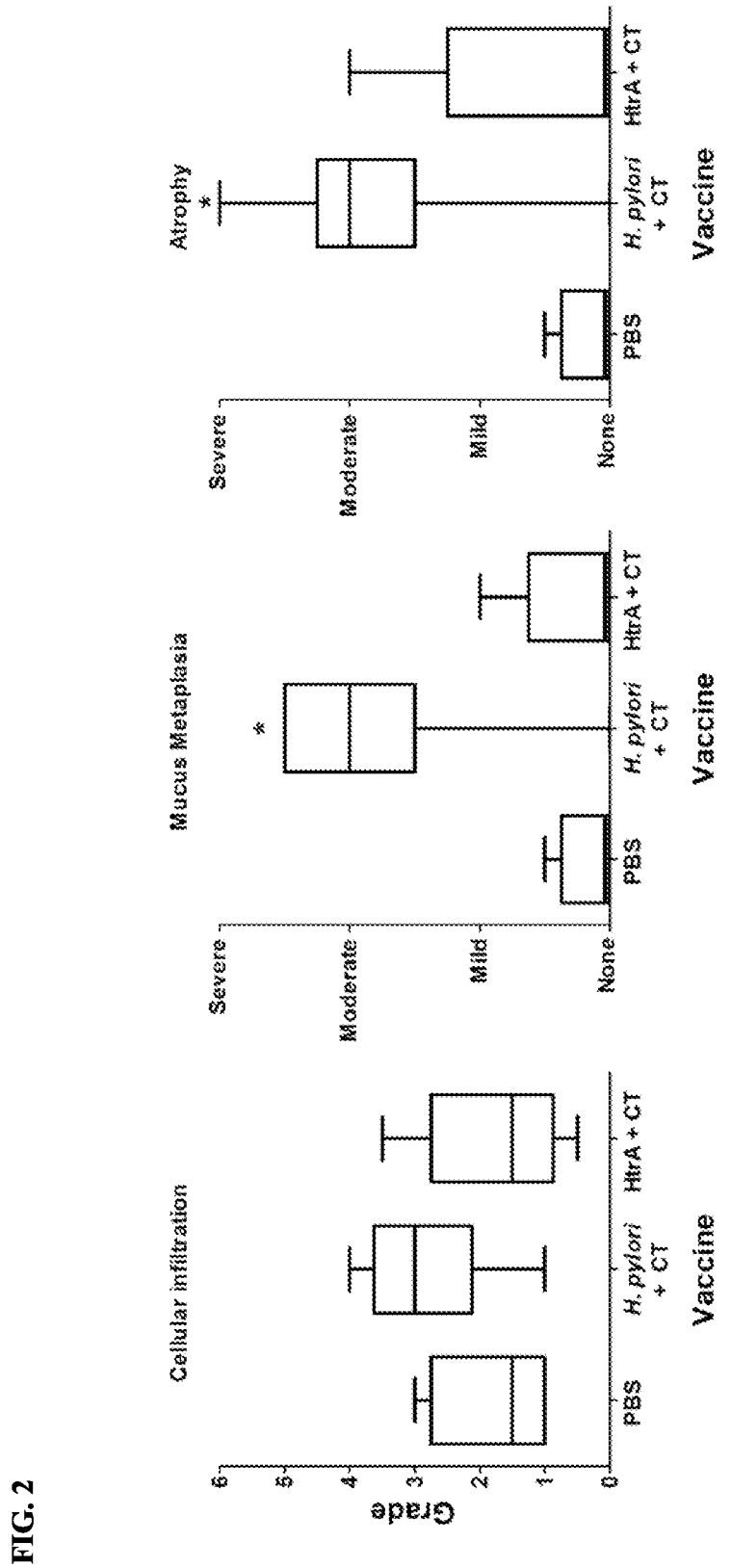
FIG. 2. Prophylactic vaccination with recombinant HtrA does not cause post-immunisation gastritis. Stomachs from the mice were assessed histologically for gastritis. As expected, mice vaccinated with killed *H. pylori* plus CT before challenge had a significantly increased severity of gastritis compared to the negative control group (*Mann-Whitney). However the gastritis in mice vaccinated with HtrA plus CT was indistinguishable from the negative control group. In other words, despite the protective immunity shown in FIG. 1, these mice were protected from developing post-immunisation gastritis.

Stomachs from the mice referred to in FIG. 1 were assessed histologically for gastritis. As expected, mice vaccinated with killed *H. pylori* plus CT before challenge had a significantly increased severity of gastritis (increased atrophy and metaplasia, key gastritis readouts) compared to the negative control group (*Mann-Whitney; FIG. 2). However the gastritis in mice vaccinated with HtrA plus CT was indistinguishable from the negative control group. In other words, despite the protective immunity shown in FIG. 1, these mice did not develop post-immunisation gastritis.

This was unlikely to be related to the slightly lower level of protection observed in the HtrA plus CT group compared to the positive control group; the present inventor has performed countless similar experiments with recombinant antigens testing *H. pylori* vaccines and not seen this previously. It is well recognised in the literature that *H. pylori* colonisation does not correlate with gastritis severity.

Suppression of Gastric Cytokine Levels Post-Immunisation

*H. pylori* infection induces a mixed Th1 and Th17 response in the gastric tissues of both mice and humans. IL-10 is known to be an important suppressor of *H. pylori*-induced gastritis. IL-13 is the main marker used for measuring Th2-type responses. To explore this reduced gastritis further, cytokines in the gastric homogenates of the above mice were quantified by ELISA.

As expected, gastric tissues from the infection control (PBS) and positive control vaccine (*H. pylori*+CT) groups presented with high levels of Th1 (IFNγ) and Th17 (IL-17A) cytokines. This particular experiment did not contain an uninfected control group, but years of experiments indicate these cytokines are not normally easily detected in gastric homogenates. IL-10 and IL-13 were also elevated; this is also expected, as these cytokines increase to suppress the inflammatory signals induced by Th1 and Th17-type cytokines.

Figure 3:
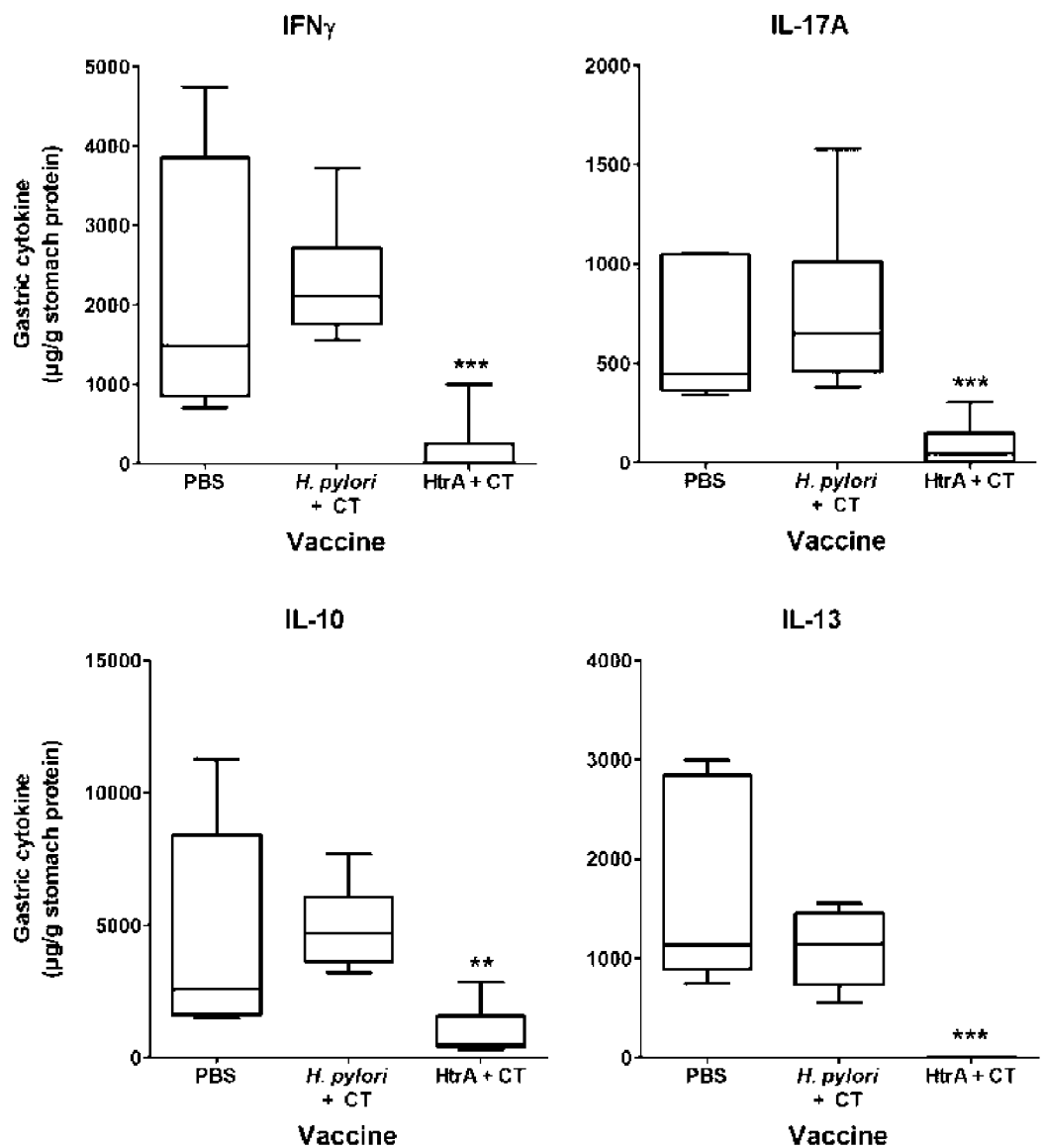
FIG. 3. Prophylactic vaccination with recombinant HtrA (rHtrA) suppresses gastric cytokine levels in response to *H. pylori* infection. Cytokine levels in the gastric tissues of the mice described in FIG. 1 were quantified by ELISA. As expected, gastric tissues from the infection control mice (PBS) and mice that received the positive control vaccine (*H. pylori*+CT) presented with high cytokine levels including those known to be highly pro-inflammatory (IFNγ and IL-17A). Unexpectedly, vaccination with HtrA+CT significantly suppressed levels of these cytokines in infected mice to extremely low or undetectable levels ($p<0.01$, *$p<0.001$; ANOVA).

The completely unexpected observation was that vaccination with HtrA+CT significantly suppressed levels of these cytokines in infected mice to extremely low or undetectable levels (p<0.01, *p<0.0001; ANOVA) (FIG. 3). This is the first time a vaccine has been demonstrated to suppress *H. pylori*-induced gastritis.

Recombinant HtrA (rHtrA) Vaccination Induces a Neutralising Antibody Response

Figure 4:
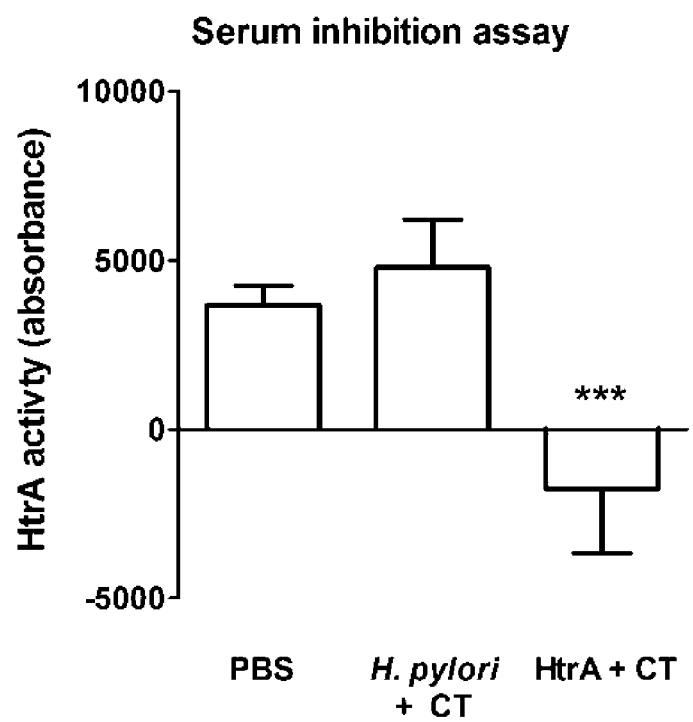
FIG. 4. Prophylactic vaccination with recombinant HtrA induces an enzyme neutralising antibody response. Sera were collected from the vaccinated/challenged mice shown in FIG. 1 at the end of the experiment (four weeks after *H. pylori* challenge). These sera were mixed with HtrA prior to measuring its proteolytic cleavage of casein. Sera from mice vaccinated with HtrA then challenged with *H. pylori* inhibited the ability of HtrA protease to cleave this protein substrate (***ANOVA), in contrast to sera from the other groups.

The present inventor hypothesized that the vaccine was suppressing gastritis and gastric cytokines levels by inducing antibodies that neutralised HtrA activity. To test this, an in vitro assay for HtrA activity was developed to assess the inhibitory ability of sera from the above mice. The results in FIG. 4 show that sera from mice vaccinated with HtrA then challenged with *H. pylori* did indeed inhibit the ability of HtrA protease to cleave a target substrate (***ANOVA). This was in contrast to sera from the other groups.

Recombinant HtrA (rHtrA) Vaccination Induces Antibodies Against HtrA

Figure 5:
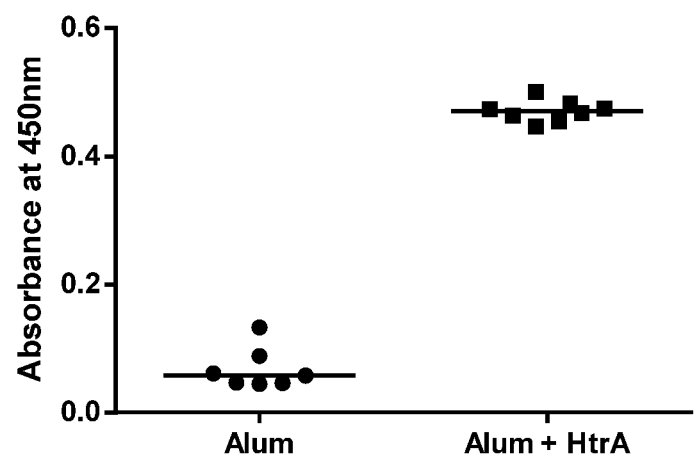
FIG. 5. Vaccination with HtrA induces serum antibodies against HtrA. A group of C57BL/6 mice (n=8) were vaccinated nasally with rHtrA plus CT. Three vaccinations were given, spaced by three weeks. A control group was sham-treated with PBS. One week after the last vaccination, mice were killed and sera collected. Antibodies against rHtrA was measured by ELISA.

A group of mice was vaccinated three times with rHtrA+CT via the nasal route. Negative controls were sham dosed with PBS. Sera from the vaccinated mice contained antibodies that specifically detected HtrA (FIG. 5).

Therapeutic HtrA Vaccination by Injection Route

Groups of mice were infected with *H. pylori* before being subcutaneously injected with either alum adjuvant alone (negative control), rHtrA and alum or rHtra$^{sa}$ and alum (rHtra$^{sa}$ is identical to rHtrA except for a single amino acid substitution of serine to alanine which makes the enzyme inactive). Four weeks after the last vaccination, stomachs were removed and bacterial colonization quantified by colony-forming assay. There was no difference in *H. pylori* colonization levels between any of the groups (FIG. 6).

Figure 6:
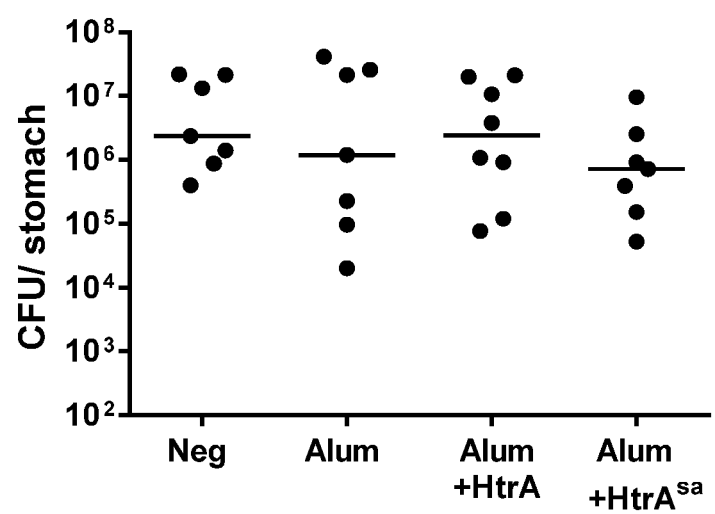
FIG. 6. Therapeutic vaccination with injected HtrA plus alum does not reduce colonization by *H. pylori*. Groups of C57BL/6 mice (n=7/8) were infected with *H. pylori* for four weeks before being subcutaneously injected with four weekly doses of either alum adjuvant alone (negative control), rHtrA and alum or rHtra$^{sa}$ and alum. Four weeks after the last vaccination, stomachs were removed and bacterial colonization quantified by colony-forming assay.
Figure 7A:
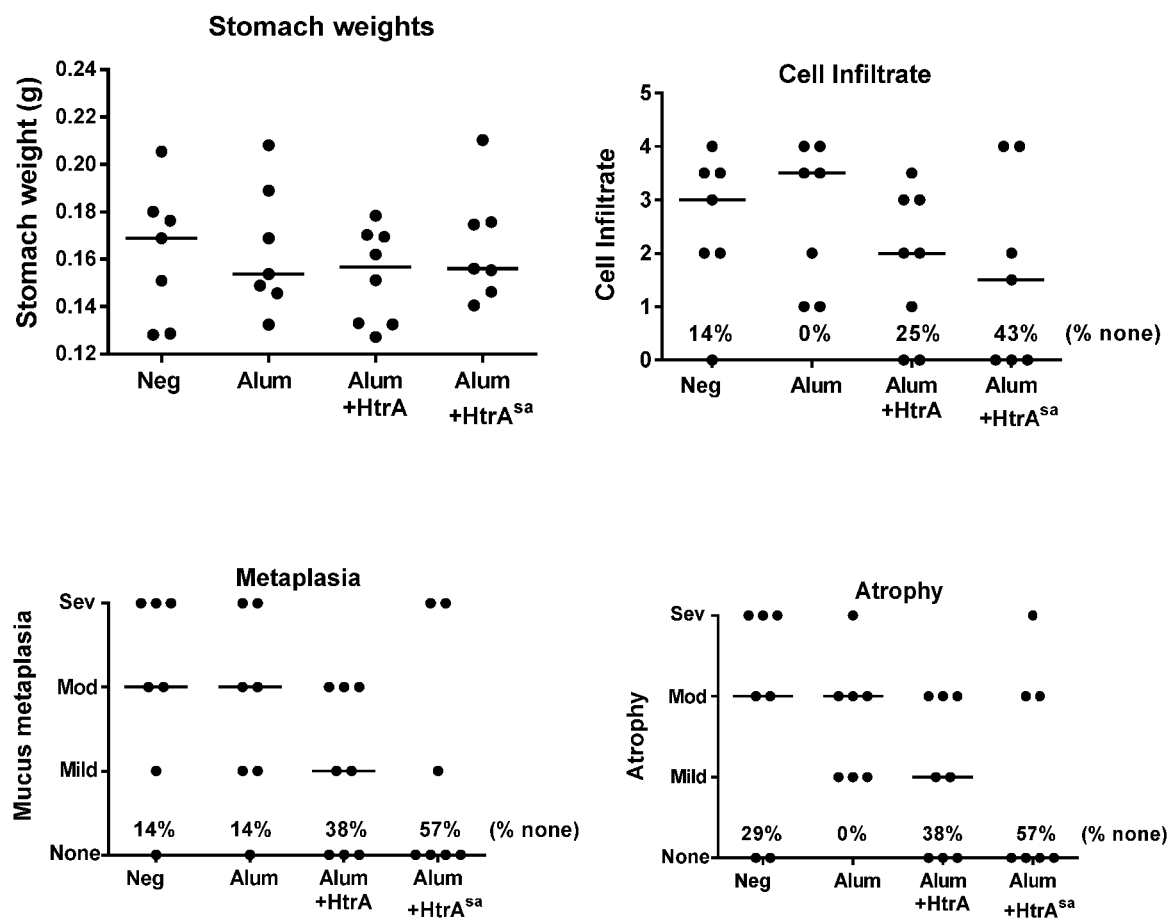
FIGS. 7A-7B. Therapeutic vaccination with injected HtrA plus alum protects against *H. pylori* induced gastritis. The severity of gastritis in stomachs of therapeutically vaccinated mice (as described in FIG. 6) were quantified histologically. A) rHtra and rHtrA$^{sa}$ groups shown separately. B) The two rHtrA groups combined. Percentages indicate the proportion of mice that had no visible cell infiltrate, metaplasia or atrophy. Despite having no effect on colonization (FIG. 6), vaccination with either active rHtra or inactive rHtrA$^{sa}$ resulted in protection against the development of *H. pylori*-induced atrophic gastritis.
Figure 7B:
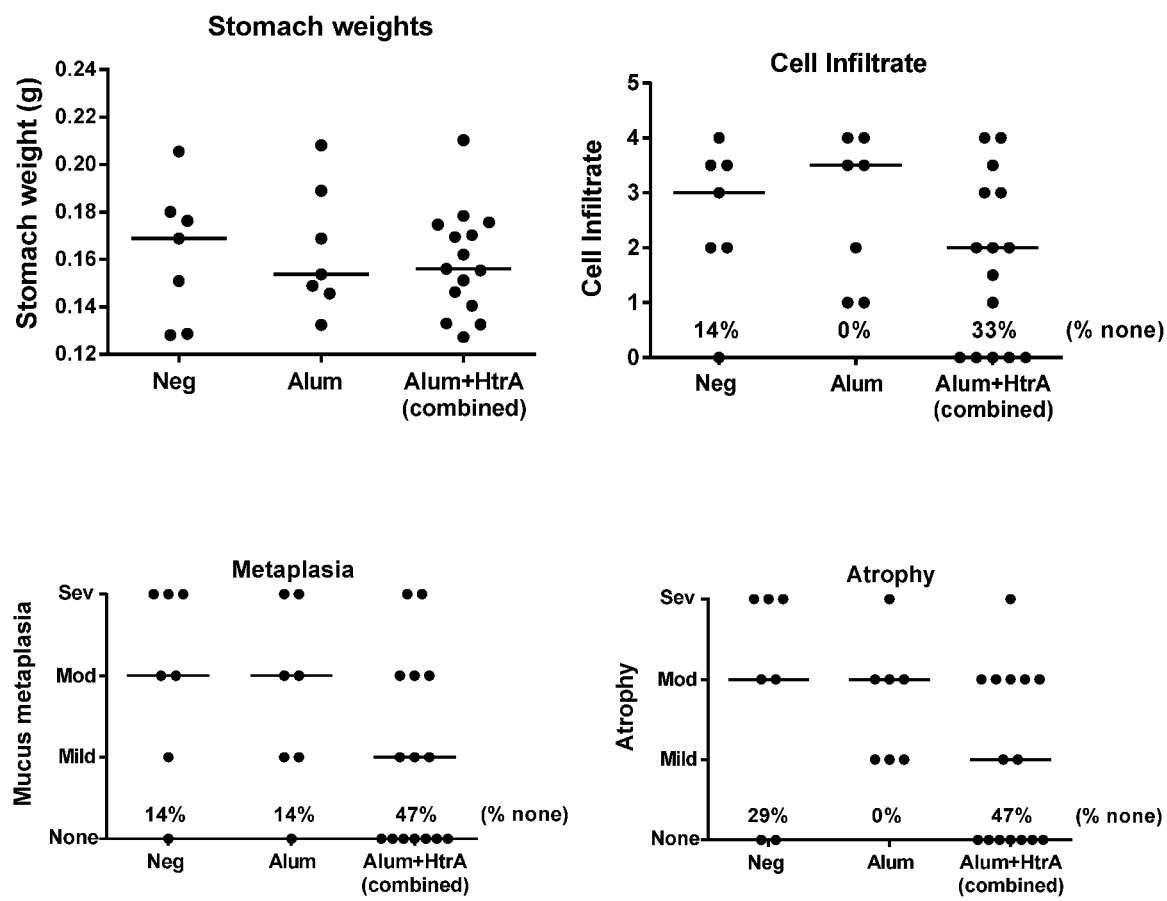

Therapeutic HtrA Vaccination by the Injection Route does Protect Against *H. pylori*-Induced Gastritis The severity of gastritis in the stomachs of therapeutically vaccinated mice described in FIG. 6 was quantified histologically. Despite having no effect on colonization (FIG. 6), vaccination with either active rHtra or inactive rHtrA$^{sa}$ resulted in protection against the development of *H. pylori*-induced atrophic gastritis. (FIGS. 7A-7B).

Figure 8:
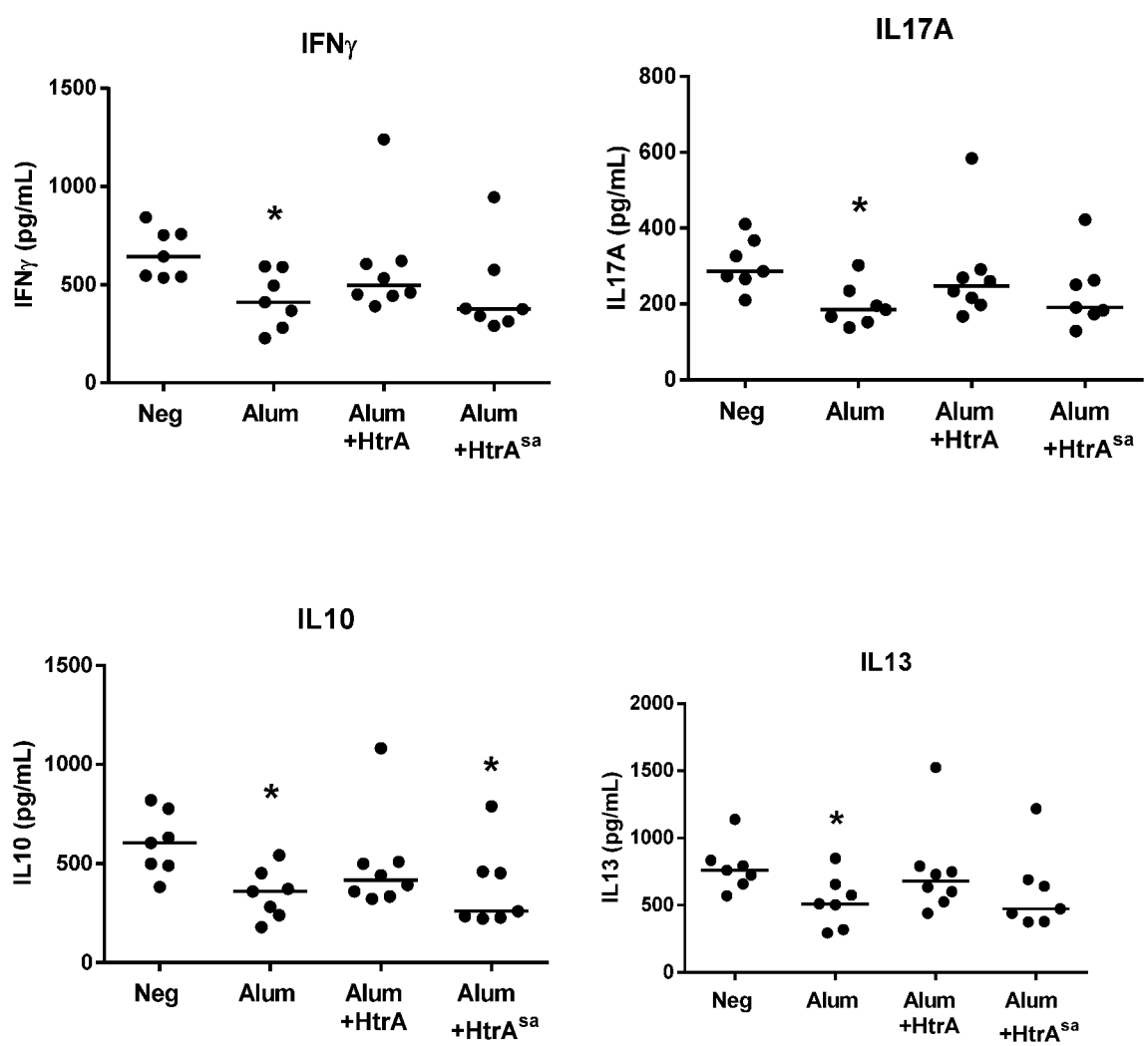
FIG. 8. Therapeutic vaccination with injected HtrA plus alum protects against *H. pylori* induced gastritis without a significant increase in gastric cytokines. Cytokine levels in the gastric homogenates from mice therapeutically vaccinated with HtrA (as described in FIG. 6) were quantified by ELISA. Vaccination with either rHtrA group produced no significant increase in key gastric cytokines, particularly compared with the main negative control group, which were vaccinated with alum alone.

Therapeutic HtrA Vaccination by the Injection Route Protects Against *H. pylori*-Induced Gastritis without a Significant Increase in Gastric Cytokines Cytokine levels in the gastric homogenates from the mice described in FIG. 6 were quantified by ELISA. Vaccination with either rHtrA group produced no significant increase in key gastric cytokines, particularly compared with the main negative control group vaccinated with alum alone (FIG. 8).

Figure 9:
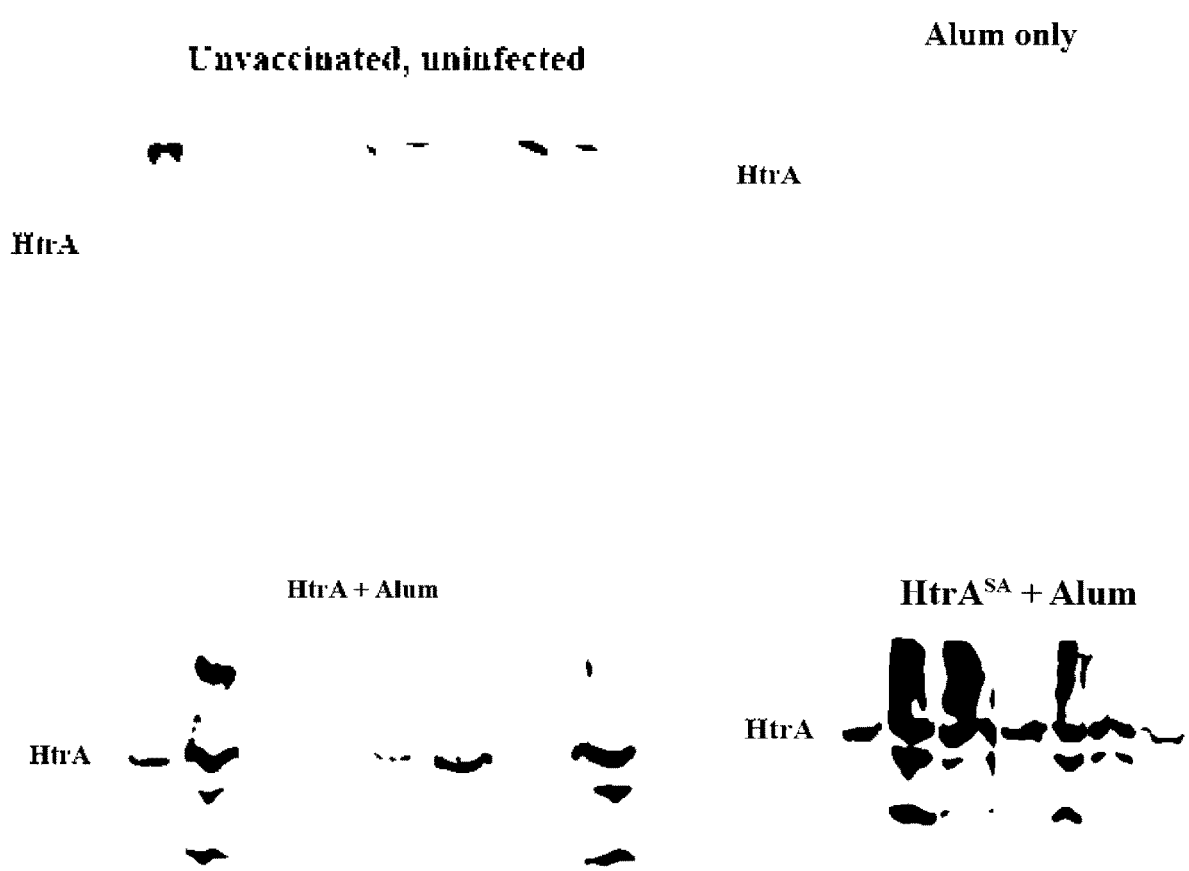
FIG. 9. Therapeutic vaccination with injected HtrA plus alum induces intestinal antibodies against native HtrA. Intestinal scrapings were collected from mice described as in FIG. 6. Antibodies binding *H. pylori* HtrA were detected by western blot. Blots are shown from negative control mice (left uninfected and unvaccinated, or infected then injected with alum alone) or *H. pylori* infected mice vaccinated with rHtrA and alum or rHtrA$^{SA}$ and alum. Lanes show blots probed with sera from individual mice.

Therapeutic rHtrA Vaccination by the Injection Route Induces Antibodies in the Gastrointestinal Tract Specific for Native HtrA Intestinal scrapings from the mice described in FIG. 6 were tested for the presence of antibodies against HtrA. Western blot analysis of intestinal scrapings against *H. pylori* lysate showed that only infected mice therapeutically vaccinate with rHtrA had detectable antibodies against HtrA (FIG. 9). Importantly this also demonstrates that vaccination with recombinant HtrA induced mucosal antibodies against native *H. pylori* HtrA.

It will be appreciated by persons skilled in the art that numerous variations and/or modifications may be made to the invention as shown in the specific embodiments without departing from the scope of the invention as broadly described. The present embodiments are, therefore, to be considered in all respects as illustrative and not restrictive.

All publications discussed and/or referenced herein are incorporated herein in their entirety.

The present application claims priority from AU 2014902493 filed 30 Jun. 2014, the entire contents of which are incorporated herein by reference.

Any discussion of documents, acts, materials, devices, articles or the like which has been included in the present specification is solely for the purpose of providing a context for the present invention. It is not to be taken as an admission that any or all of these matters form part of the prior art base or were common general knowledge in the field relevant to the present invention as it existed before the priority date of each claim of this application.

---

The invention claimed is:

1. A method of treating *Helicobacter pylori*-bacteria induced gastritis in a subject, the method comprising administering to the subject a bacterial HtrA polypeptide, wherein the bacterial HtrA polypeptide comprises SEQ ID NO:1.

2. The method of claim 1, wherein the bacterial HtrA polypeptide is administered in a pharmaceutical composition comprising a pharmaceutically acceptable excipient and/or adjuvant.

3. The method of claim 1, wherein the gastritis is atrophic gastritis.

4. The method of claim 1, wherein the bacterial HtrA polypeptide consists of SEQ ID NO:1.

* * * * *

SEQUENCE LISTING

```
<160> NUMBER OF SEQ ID NOS: 40

<210> SEQ ID NO 1
<211> LENGTH: 475
<212> TYPE: PRT
<213> ORGANISM: Helicobacter pylori

<400> SEQUENCE: 1

Met Lys Lys Thr Leu Phe Ile Ser Leu Ala Leu Ala Leu Ser Leu Asn
1               5                   10                  15

Ala Gly Asn Ile Gln Ile Gln Ser Met Pro Lys Val Lys Glu Arg Val
            20                  25                  30

Ser Val Pro Ser Lys Asp Asp Thr Ile Tyr Ser Tyr His Asp Ser Ile
        35                  40                  45

Lys Asp Ser Ile Lys Ala Val Val Asn Ile Ser Thr Glu Lys Lys Ile
    50                  55                  60

Lys Asn Asn Phe Ile Gly Gly Val Phe Asn Asp Pro Phe Phe Gln
65                  70                  75                  80

Gln Phe Phe Gly Asp Leu Gly Gly Met Ile Pro Lys Glu Arg Met Glu
                85                  90                  95

Arg Ala Leu Gly Ser Gly Val Ile Ile Ser Lys Asp Gly Tyr Ile Val
            100                 105                 110

Thr Asn Asn His Val Ile Asp Gly Ala Asp Lys Ile Lys Val Thr Ile
        115                 120                 125

Pro Gly Ser Asn Lys Glu Tyr Ser Ala Thr Leu Val Gly Thr Asp Ser
    130                 135                 140

Glu Ser Asp Leu Ala Val Ile Arg Ile Thr Lys Asp Asn Leu Pro Thr
145                 150                 155                 160

Ile Lys Phe Ser Asp Ser Asn Asp Ile Ser Val Gly Asp Leu Val Phe
                165                 170                 175

Ala Ile Gly Asn Pro Phe Gly Val Gly Glu Ser Val Thr Gln Gly Ile
            180                 185                 190

Val Ser Ala Leu Asn Lys Ser Gly Ile Gly Ile Asn Ser Tyr Glu Asn
        195                 200                 205

Phe Ile Gln Thr Asp Ala Ser Ile Asn Pro Gly Asn Ser Gly Gly Ala
    210                 215                 220

Leu Ile Asp Ser Arg Gly Gly Leu Val Gly Ile Asn Thr Ala Ile Ile
225                 230                 235                 240

Ser Lys Thr Gly Gly Asn His Gly Ile Gly Phe Ala Ile Pro Ser Asn
                245                 250                 255

Met Val Lys Asp Thr Val Thr Gln Leu Ile Lys Thr Gly Lys Ile Glu
```

```
                        260                 265                 270
Arg Gly Tyr Leu Gly Val Gly Leu Gln Asp Leu Ser Gly Asp Leu Gln
                275                 280                 285

Asn Ser Tyr Asp Asn Lys Glu Gly Ala Val Val Ile Ser Val Glu Lys
            290                 295                 300

Asp Ser Pro Ala Lys Lys Ala Gly Ile Leu Val Trp Asp Leu Ile Thr
305                 310                 315                 320

Glu Val Asn Gly Lys Lys Val Lys Asn Thr Asn Glu Leu Arg Asn Leu
                325                 330                 335

Ile Gly Ser Met Leu Pro Asn Gln Arg Val Thr Leu Lys Val Ile Arg
                340                 345                 350

Asp Lys Lys Glu Arg Ala Phe Thr Leu Thr Leu Ala Glu Arg Lys Asn
            355                 360                 365

Pro Asn Lys Lys Glu Thr Ile Ser Ala Gln Asn Gly Ala Gln Gly Gln
            370                 375                 380

Leu Asn Gly Leu Gln Val Glu Asp Leu Thr Gln Glu Thr Lys Arg Ser
385                 390                 395                 400

Met Arg Leu Ser Asp Asp Val Gln Gly Val Leu Val Ser Gln Val Asn
                405                 410                 415

Glu Asn Ser Pro Ala Glu Gln Ala Gly Phe Arg Gln Gly Asn Ile Ile
            420                 425                 430

Thr Lys Ile Glu Glu Val Glu Val Lys Ser Val Ala Asp Phe Asn His
            435                 440                 445

Ala Leu Glu Lys Tyr Lys Gly Lys Pro Lys Arg Phe Leu Val Leu Asp
        450                 455                 460

Leu Asn Gln Gly Tyr Arg Ile Ile Leu Val Lys
465                 470                 475

<210> SEQ ID NO 2
<211> LENGTH: 476
<212> TYPE: PRT
<213> ORGANISM: Helicobacter pylori

<400> SEQUENCE: 2

Met Met Lys Lys Thr Leu Phe Val Ser Leu Ala Leu Ala Leu Ser Leu
1               5                   10                  15

Asn Ala Gly Asn Ile Gln Ile Gln Asn Met Pro Lys Val Lys Glu Arg
            20                  25                  30

Ile Ser Val Pro Ser Lys Asp Asp Thr Ile Tyr Ser Tyr His Asp Ser
        35                  40                  45

Ile Lys Asp Ser Ile Lys Ala Val Val Asn Ile Ser Thr Glu Lys Lys
    50                  55                  60

Ile Lys Asn Asn Phe Ile Gly Gly Gly Val Phe Asn Asp Pro Phe Phe
65                  70                  75                  80

Gln Gln Phe Phe Gly Asp Leu Gly Gly Met Ile Pro Lys Glu Arg Met
                85                  90                  95

Glu Arg Ala Leu Gly Ser Gly Val Ile Ile Ser Lys Asp Gly Tyr Ile
            100                 105                 110

Val Thr Asn Asn His Val Ile Asp Gly Ala Asp Lys Ile Lys Val Thr
        115                 120                 125

Ile Pro Gly Ser Asn Lys Glu Tyr Ser Ala Thr Leu Val Gly Thr Asp
    130                 135                 140

Ser Glu Ser Asp Leu Ala Val Ile Arg Ile Thr Lys Asp Asn Leu Pro
145                 150                 155                 160
```

Thr Ile Lys Phe Ser Asp Ser Asn Asp Ile Leu Val Gly Asp Leu Val
            165                 170                 175

Phe Ala Ile Gly Asn Pro Phe Val Gly Glu Ser Val Thr Gln Gly
        180                 185                 190

Ile Val Ser Ala Leu Asn Lys Ser Gly Ile Gly Ile Asn Ser Tyr Glu
            195                 200                 205

Asn Phe Ile Gln Thr Asp Ala Ser Ile Asn Pro Gly Asn Ser Gly Gly
    210                 215                 220

Ala Leu Ile Asp Ser Arg Gly Gly Leu Val Gly Ile Asn Thr Ala Ile
225                 230                 235                 240

Ile Ser Lys Thr Gly Gly Asn His Gly Ile Gly Phe Ala Ile Pro Ser
            245                 250                 255

Asn Met Val Lys Asp Ile Val Thr Gln Leu Ile Lys Thr Gly Lys Ile
            260                 265                 270

Glu Arg Gly Tyr Leu Gly Val Gly Leu Gln Asp Leu Ser Gly Asp Leu
            275                 280                 285

Gln Asn Ser Tyr Asp Asn Lys Glu Gly Ala Val Val Ile Ser Val Glu
    290                 295                 300

Lys Asp Ser Pro Ala Lys Lys Ala Gly Ile Leu Val Trp Asp Leu Ile
305                 310                 315                 320

Thr Glu Val Asn Gly Lys Lys Val Lys Asn Thr Asn Glu Leu Arg Asn
            325                 330                 335

Leu Ile Gly Ser Met Leu Pro Asn Gln Arg Val Thr Leu Lys Val Ile
            340                 345                 350

Arg Asp Lys Lys Glu Arg Ala Phe Thr Leu Thr Leu Ala Glu Arg Lys
            355                 360                 365

Asn Pro Asn Lys Lys Glu Thr Ile Ser Ala Gln Asn Gly Thr Gln Gly
    370                 375                 380

Gln Leu Asn Gly Leu Gln Val Glu Asp Leu Thr Gln Lys Thr Lys Arg
385                 390                 395                 400

Ser Met Arg Leu Ser Asp Val Gln Gly Val Leu Val Ser Gln Val
            405                 410                 415

Asn Glu Asn Ser Pro Ala Glu Gln Ala Gly Phe Arg Gln Gly Asn Ile
            420                 425                 430

Ile Thr Lys Ile Glu Glu Ile Glu Val Lys Ser Val Ala Asp Phe Asn
            435                 440                 445

His Ala Leu Glu Lys Tyr Lys Gly Lys Pro Lys Arg Phe Leu Val Leu
    450                 455                 460

Asp Leu Asn Gln Gly Tyr Arg Ile Ile Leu Val Lys
465                 470                 475

<210> SEQ ID NO 3
<211> LENGTH: 476
<212> TYPE: PRT
<213> ORGANISM: Helicobacter pylori

<400> SEQUENCE: 3

Met Met Lys Lys Thr Leu Phe Ile Ser Leu Ala Leu Ala Leu Ser Leu
1               5                   10                  15

Asn Ala Gly Asn Ile Gln Ile Gln Asn Met Pro Lys Val Lys Glu Arg
            20                  25                  30

Val Ser Val Pro Ser Lys Asp Asp Thr Ile Tyr Ser Tyr His Asp Ser
        35                  40                  45

Ile Lys Asp Ser Ile Lys Ala Val Val Asn Ile Ser Thr Glu Lys Lys
    50                  55                  60

```
Ile Lys Asn Asn Phe Ile Gly Gly Val Phe Asn Asp Pro Phe Phe
 65                  70                  75                  80

Gln Gln Phe Phe Gly Asp Leu Gly Gly Met Ile Pro Lys Glu Arg Met
             85                  90                  95

Glu Arg Ala Leu Gly Ser Gly Val Ile Ile Ser Lys Asp Gly Tyr Ile
            100                 105                 110

Val Thr Asn Asn His Val Ile Asp Gly Ala Asp Lys Ile Lys Val Thr
            115                 120                 125

Ile Pro Gly Ser Asn Lys Glu Tyr Ser Ala Thr Leu Val Gly Thr Asp
            130                 135                 140

Ser Glu Ser Asp Leu Ala Val Ile Arg Ile Thr Lys Asn Leu Pro
145                 150                 155                 160

Thr Ile Lys Phe Ser Asp Ser Asn Asp Ile Leu Val Gly Asp Leu Val
                165                 170                 175

Phe Ala Ile Gly Asn Pro Phe Gly Val Gly Glu Ser Val Thr Gln Gly
            180                 185                 190

Ile Val Ser Ala Leu Asn Lys Ser Gly Ile Gly Ile Asn Ser Tyr Glu
            195                 200                 205

Asn Phe Ile Gln Thr Asp Ala Ser Ile Asn Pro Gly Asn Ser Gly Gly
            210                 215                 220

Ala Leu Ile Asp Ser Arg Gly Gly Leu Val Gly Ile Asn Thr Ala Ile
225                 230                 235                 240

Ile Ser Lys Thr Gly Gly Asn His Gly Ile Gly Phe Ala Ile Pro Ser
                245                 250                 255

Asn Met Val Lys Asp Ile Val Thr Gln Leu Ile Lys Thr Gly Lys Ile
            260                 265                 270

Glu Arg Gly Tyr Leu Gly Val Gly Leu Gln Asp Leu Ser Gly Asp Leu
            275                 280                 285

Gln Asn Ser Tyr Asp Asn Lys Glu Gly Ala Val Val Ile Ser Val Glu
            290                 295                 300

Lys Asp Ser Pro Ala Lys Lys Ala Gly Ile Leu Val Trp Asp Leu Ile
305                 310                 315                 320

Thr Glu Val Asn Gly Lys Lys Val Lys Asn Thr Asn Glu Leu Arg Asn
                325                 330                 335

Leu Ile Gly Ser Met Leu Pro Asn Gln Arg Val Thr Leu Lys Val Ile
            340                 345                 350

Arg Asp Lys Lys Glu Arg Thr Phe Thr Leu Thr Leu Ala Glu Arg Lys
            355                 360                 365

Asn Pro Asn Lys Lys Glu Thr Ile Ser Ala Gln Asn Gly Ala Gln Gly
            370                 375                 380

Gln Leu Asn Gly Leu Gln Val Glu Asp Leu Thr Gln Lys Thr Lys Arg
385                 390                 395                 400

Ser Met Arg Leu Ser Asp Asp Val Gln Gly Val Leu Val Ser Gln Val
                405                 410                 415

Asn Glu Asn Ser Pro Ala Glu Gln Ala Gly Phe Arg Gln Gly Asn Ile
            420                 425                 430

Ile Thr Lys Ile Glu Glu Ile Glu Val Lys Ser Val Ala Asp Phe Asn
            435                 440                 445

His Ala Leu Glu Lys Tyr Lys Gly Lys Pro Lys Arg Phe Leu Val Leu
            450                 455                 460

Asp Leu Asn Gln Gly Tyr Arg Ile Ile Leu Val Lys
465                 470                 475
```

<210> SEQ ID NO 4
<211> LENGTH: 476
<212> TYPE: PRT
<213> ORGANISM: Helicobacter pylori

<400> SEQUENCE: 4

```
Met Met Lys Lys Thr Leu Phe Ile Ser Leu Ala Leu Ala Leu Ser Leu
1               5                   10                  15

Asn Ala Gly Asn Ile Gln Ile Gln Asn Met Pro Lys Val Lys Glu Arg
            20                  25                  30

Ile Ser Val Pro Ser Lys Glu Asp Thr Ile Tyr Ser Tyr His Asp Ser
        35                  40                  45

Ile Lys Asp Ser Ile Lys Ala Val Val Asn Ile Ser Thr Glu Lys Lys
    50                  55                  60

Ile Lys Asn Asn Phe Ile Gly Gly Val Phe Asn Asp Pro Phe Phe
65                  70                  75                  80

Gln Gln Phe Phe Gly Asp Leu Gly Gly Met Ile Pro Lys Glu Arg Met
                85                  90                  95

Glu Arg Ala Leu Gly Ser Gly Val Ile Ile Ser Lys Asp Gly Tyr Ile
            100                 105                 110

Val Thr Asn Asn His Val Ile Asp Gly Ala Asp Lys Ile Lys Val Thr
        115                 120                 125

Ile Pro Gly Ser Asn Lys Glu Tyr Ser Ala Thr Leu Val Gly Thr Asp
    130                 135                 140

Ser Glu Ser Asp Leu Ala Val Ile Arg Ile Thr Lys Asp Asn Leu Pro
145                 150                 155                 160

Thr Ile Lys Phe Ser Asp Ser Asn Asp Ile Leu Val Gly Asp Leu Val
                165                 170                 175

Phe Ala Ile Gly Asn Pro Phe Gly Val Gly Glu Ser Val Thr Gln Gly
            180                 185                 190

Ile Val Ser Ala Leu Asn Lys Ser Gly Ile Gly Ile Asn Ser Tyr Glu
        195                 200                 205

Asn Phe Ile Gln Thr Asp Ala Ser Ile Asn Pro Gly Asn Ser Gly Gly
    210                 215                 220

Ala Leu Ile Asp Ser Arg Gly Gly Leu Val Gly Ile Asn Thr Ala Ile
225                 230                 235                 240

Ile Ser Lys Thr Gly Gly Asn His Gly Ile Gly Phe Ala Ile Pro Ser
                245                 250                 255

Asn Met Val Lys Asp Ile Val Thr Gln Leu Ile Lys Thr Gly Lys Ile
            260                 265                 270

Glu Arg Gly Tyr Leu Gly Val Gly Leu Gln Asp Leu Ser Gly Asp Leu
        275                 280                 285

Gln Asn Ser Tyr Asp Asn Lys Glu Gly Ala Val Val Ile Ser Val Glu
    290                 295                 300

Lys Asp Ser Pro Ala Lys Lys Ala Gly Ile Leu Val Trp Asp Leu Ile
305                 310                 315                 320

Thr Glu Val Asn Gly Lys Lys Val Lys Asn Thr Asn Glu Leu Arg Asn
                325                 330                 335

Leu Ile Gly Ser Met Leu Pro Asn Gln Arg Val Thr Leu Lys Val Ile
            340                 345                 350

Arg Asp Lys Lys Glu Arg Thr Phe Thr Leu Thr Leu Ala Glu Arg Lys
        355                 360                 365

Asn Pro Asn Lys Lys Glu Thr Ile Ser Ala Gln Asn Gly Val Gln Gly
    370                 375                 380
```

```
Gln Leu Asn Gly Leu Gln Val Glu Asp Leu Thr Gln Lys Thr Lys Arg
385                 390                 395                 400

Ser Met Arg Leu Ser Asp Val Gln Gly Val Leu Val Ser Gln Val
            405                 410                 415

Asn Glu Asn Ser Pro Ala Glu Gln Ala Gly Phe Arg Gln Gly Asn Ile
                420                 425                 430

Ile Thr Lys Ile Glu Glu Ile Glu Val Lys Ser Val Ala Asp Phe Asn
            435                 440                 445

His Ala Leu Glu Lys Tyr Lys Gly Lys Pro Lys Arg Phe Leu Val Leu
        450                 455                 460

Asp Leu Asn Gln Gly Tyr Arg Ile Ile Leu Val Lys
465                 470                 475

<210> SEQ ID NO 5
<211> LENGTH: 476
<212> TYPE: PRT
<213> ORGANISM: Helicobacter pylori

<400> SEQUENCE: 5

Met Met Lys Lys Thr Leu Phe Val Ser Leu Ala Leu Ala Leu Ser Leu
1               5                   10                  15

Asn Ala Gly Asn Ile Gln Ile Gln Asn Met Pro Lys Val Lys Glu Arg
            20                  25                  30

Ile Ser Val Pro Ser Lys Asp Thr Ile Tyr Ser Tyr His Asp Ser
        35                  40                  45

Ile Lys Asp Ser Ile Lys Ala Val Val Asn Ile Ser Thr Glu Lys Lys
    50                  55                  60

Ile Lys Asn Asn Phe Ile Gly Gly Val Phe Asn Asp Pro Phe Phe
65              70                  75                  80

Gln Gln Phe Phe Gly Asp Leu Gly Met Ile Pro Lys Glu Arg Met
                85                  90                  95

Glu Arg Ala Leu Gly Ser Gly Val Ile Ile Ser Lys Asp Gly Tyr Ile
            100                 105                 110

Val Thr Asn Asn His Val Ile Asp Gly Ala Asp Lys Ile Lys Val Thr
        115                 120                 125

Ile Pro Gly Ser Asn Lys Glu Tyr Ser Ala Thr Leu Val Gly Thr Asp
    130                 135                 140

Ser Glu Ser Asp Leu Ala Val Ile Arg Ile Thr Lys Asp Asn Leu Pro
145                 150                 155                 160

Thr Ile Lys Phe Ser Asp Ser Asn Asp Ile Leu Val Gly Asp Leu Val
                165                 170                 175

Phe Ala Ile Gly Asn Pro Phe Gly Val Gly Glu Ser Val Thr Gln Gly
            180                 185                 190

Ile Val Ser Ala Leu Asn Lys Ser Gly Ile Gly Ile Asn Ser Tyr Glu
        195                 200                 205

Asn Phe Ile Gln Thr Asp Ala Ser Ile Asn Pro Gly Asn Ser Gly Gly
    210                 215                 220

Ala Leu Ile Asp Ser Arg Gly Gly Leu Val Gly Ile Asn Thr Ala Ile
225                 230                 235                 240

Ile Ser Lys Thr Gly Gly Asn His Gly Ile Gly Phe Ala Ile Pro Ser
                245                 250                 255

Asn Met Val Lys Asp Ile Val Thr Gln Leu Ile Lys Thr Gly Lys Ile
            260                 265                 270

Glu Arg Gly Tyr Leu Gly Val Gly Leu Gln Asp Leu Ser Gly Asp Leu
```

```
                    275                 280                 285
Gln Asn Ser Tyr Asp Asn Lys Glu Gly Ala Val Val Ile Ser Val Glu
290                 295                 300

Lys Asp Ser Pro Ala Lys Ala Gly Ile Leu Val Trp Asp Leu Ile
305                 310                 315                 320

Thr Glu Val Asn Gly Lys Lys Val Lys Asn Thr Asn Glu Leu Arg Asn
                    325                 330                 335

Leu Ile Gly Ser Met Leu Pro Asn Gln Arg Val Thr Leu Lys Ile Ile
                340                 345                 350

Arg Asp Lys Lys Glu Arg Thr Phe Thr Leu Thr Leu Ala Glu Arg Lys
                    355                 360                 365

Asn Pro Asn Lys Lys Glu Thr Ile Ser Ala Gln Asn Gly Ala Gln Gly
            370                 375                 380

Gln Leu Asn Gly Leu Gln Val Glu Asp Leu Thr Gln Lys Thr Lys Arg
385                 390                 395                 400

Ser Met Arg Leu Ser Asp Asp Val Gln Gly Val Leu Val Ser Gln Val
                405                 410                 415

Asn Glu Asn Ser Pro Ala Glu Gln Ala Gly Phe Arg Gln Gly Asn Ile
            420                 425                 430

Ile Thr Lys Ile Glu Glu Ile Glu Val Lys Ser Val Ala Asp Phe Asn
                435                 440                 445

His Ala Leu Glu Lys Tyr Lys Gly Lys Pro Lys Arg Phe Leu Val Leu
        450                 455                 460

Asp Leu Asn Gln Gly Tyr Arg Ile Ile Leu Val Lys
465                 470                 475

<210> SEQ ID NO 6
<211> LENGTH: 476
<212> TYPE: PRT
<213> ORGANISM: Helicobacter pylori

<400> SEQUENCE: 6

Met Met Lys Lys Thr Phe Phe Val Ser Leu Ala Leu Ala Leu Ser Leu
1               5                   10                  15

Asn Ala Gly Asn Ile Gln Ile Gln Asn Met Pro Lys Val Lys Glu Arg
                20                  25                  30

Val Ser Val Pro Ser Lys Asp Asp Thr Ile Tyr Ser Tyr His Asp Ser
            35                  40                  45

Ile Lys Asp Ser Ile Lys Ala Val Val Asn Ile Ser Thr Glu Lys Lys
        50                  55                  60

Ile Lys Asn Asn Phe Ile Gly Gly Gly Val Phe Asn Asp Pro Phe Phe
65                  70                  75                  80

Gln Gln Phe Phe Gly Asp Leu Gly Gly Met Ile Pro Lys Glu Arg Met
                85                  90                  95

Glu Arg Ala Leu Gly Ser Gly Val Ile Ile Ser Lys Asp Gly Tyr Ile
            100                 105                 110

Val Thr Asn Asn His Val Ile Asp Gly Ala Asp Lys Ile Lys Val Thr
        115                 120                 125

Ile Pro Gly Ser Asn Lys Glu Tyr Ser Ala Thr Leu Val Gly Thr Asp
    130                 135                 140

Ser Glu Ser Asp Leu Ala Val Ile Arg Ile Thr Lys Asp Asn Leu Pro
145                 150                 155                 160

Thr Ile Lys Phe Ser Asp Ser Asn Asp Ile Leu Val Gly Asp Leu Val
                165                 170                 175
```

```
Phe Ala Ile Gly Asn Pro Phe Gly Val Glu Ser Val Thr Gln Gly
                180                 185                 190

Ile Val Ser Ala Leu Asn Lys Ser Gly Ile Gly Ile Asn Ser Tyr Glu
            195                 200                 205

Asn Phe Ile Gln Thr Asp Ala Ser Ile Asn Pro Gly Asn Ser Gly Gly
    210                 215                 220

Ala Leu Ile Asp Ser Arg Gly Gly Leu Val Gly Ile Asn Thr Ala Ile
225                 230                 235                 240

Ile Ser Lys Thr Gly Gly Asn His Gly Ile Gly Phe Ala Ile Pro Ser
                245                 250                 255

Asn Met Val Lys Asp Ile Val Thr Gln Leu Ile Lys Thr Gly Lys Ile
            260                 265                 270

Glu Arg Gly Tyr Leu Gly Val Gly Leu Gln Asp Leu Ser Gly Asp Leu
        275                 280                 285

Gln Asn Ser Tyr Asp Asn Lys Glu Gly Ala Val Val Ile Ser Val Glu
    290                 295                 300

Lys Asp Ser Pro Ala Lys Lys Ala Gly Ile Leu Val Trp Asp Leu Ile
305                 310                 315                 320

Thr Glu Val Asn Gly Lys Lys Ile Lys Asn Thr Asn Glu Leu Arg Asn
                325                 330                 335

Leu Ile Gly Ser Met Leu Pro Asn Gln Arg Val Thr Leu Lys Val Ile
            340                 345                 350

Arg Asp Lys Lys Glu Arg Thr Phe Thr Leu Thr Leu Ala Glu Arg Lys
        355                 360                 365

Asn Pro Asn Lys Lys Glu Thr Ile Ser Ala Gln Asn Gly Ala Gln Gly
    370                 375                 380

Gln Leu Asn Gly Leu Gln Val Glu Asp Leu Thr Gln Lys Thr Lys Arg
385                 390                 395                 400

Ser Met Arg Leu Ser Asp Asp Val Gln Gly Val Leu Val Ser Gln Val
                405                 410                 415

Asn Glu Asn Ser Pro Ala Glu Gln Ala Gly Phe Arg Gln Gly Asn Ile
            420                 425                 430

Ile Thr Lys Ile Glu Glu Ile Glu Val Lys Ser Val Ala Asp Phe Asn
        435                 440                 445

His Ala Leu Glu Lys Tyr Lys Gly Lys Pro Lys Arg Phe Leu Val Leu
    450                 455                 460

Asp Leu Asn Gln Gly Tyr Arg Ile Ile Leu Val Lys
465                 470                 475

<210> SEQ ID NO 7
<211> LENGTH: 10
<212> TYPE: PRT
<213> ORGANISM: Helicobacter pylori

<400> SEQUENCE: 7

Gly Ser Asn Lys Glu Tyr Ser Ala Thr Leu
1               5                   10

<210> SEQ ID NO 8
<211> LENGTH: 10
<212> TYPE: PRT
<213> ORGANISM: Helicobacter pylori

<400> SEQUENCE: 8

Met Met Lys Lys Thr Leu Phe Ile Ser Leu
1               5                   10
```

```
<210> SEQ ID NO 9
<211> LENGTH: 10
<212> TYPE: PRT
<213> ORGANISM: Helicobacter pylori

<400> SEQUENCE: 9

Val Ser Ala Leu Asn Lys Ser Gly Ile Gly
1               5                   10

<210> SEQ ID NO 10
<211> LENGTH: 10
<212> TYPE: PRT
<213> ORGANISM: Helicobacter pylori

<400> SEQUENCE: 10

Gly Lys Lys Val Lys Asn Thr Asn Glu Leu
1               5                   10

<210> SEQ ID NO 11
<211> LENGTH: 10
<212> TYPE: PRT
<213> ORGANISM: Helicobacter pylori

<400> SEQUENCE: 11

Ile Ser Val Glu Lys Asp Ser Pro Ala Lys
1               5                   10

<210> SEQ ID NO 12
<211> LENGTH: 10
<212> TYPE: PRT
<213> ORGANISM: Helicobacter pylori

<400> SEQUENCE: 12

Thr Leu Lys Val Ile Arg Asp Lys Lys Glu
1               5                   10

<210> SEQ ID NO 13
<211> LENGTH: 10
<212> TYPE: PRT
<213> ORGANISM: Helicobacter pylori

<400> SEQUENCE: 13

Glu Asn Ser Pro Ala Glu Gln Ala Gly Phe
1               5                   10

<210> SEQ ID NO 14
<211> LENGTH: 10
<212> TYPE: PRT
<213> ORGANISM: Helicobacter pylori

<400> SEQUENCE: 14

Gln Asn Gly Thr Gln Gly Gln Leu Asn Gly
1               5                   10

<210> SEQ ID NO 15
<211> LENGTH: 10
<212> TYPE: PRT
<213> ORGANISM: Helicobacter pylori

<400> SEQUENCE: 15

Met Met Lys Lys Thr Leu Phe Val Ser Leu
1               5                   10

<210> SEQ ID NO 16
```

```
<211> LENGTH: 10
<212> TYPE: PRT
<213> ORGANISM: Helicobacter pylori

<400> SEQUENCE: 16

Gln Lys Thr Lys Arg Ser Met Arg Leu Ser
1               5                   10

<210> SEQ ID NO 17
<211> LENGTH: 10
<212> TYPE: PRT
<213> ORGANISM: Helicobacter pylori

<400> SEQUENCE: 17

Asn Pro Phe Gly Val Gly Glu Ser Val Thr
1               5                   10

<210> SEQ ID NO 18
<211> LENGTH: 10
<212> TYPE: PRT
<213> ORGANISM: Helicobacter pylori

<400> SEQUENCE: 18

Gly Gly Leu Val Gly Ile Asn Thr Ala Ile
1               5                   10

<210> SEQ ID NO 19
<211> LENGTH: 20
<212> TYPE: PRT
<213> ORGANISM: Helicobacter pylori

<400> SEQUENCE: 19

Asn Asp Pro Phe Phe Gln Gln Phe Phe Gly Asp Leu Gly Gly Met Ile
1               5                   10                  15

Pro Lys Glu Arg
            20

<210> SEQ ID NO 20
<211> LENGTH: 20
<212> TYPE: PRT
<213> ORGANISM: Helicobacter pylori

<400> SEQUENCE: 20

Met Met Lys Lys Thr Phe Phe Val Ser Leu Ala Leu Ala Leu Ser Leu
1               5                   10                  15

Asn Ala Gly Asn
            20

<210> SEQ ID NO 21
<211> LENGTH: 20
<212> TYPE: PRT
<213> ORGANISM: Helicobacter pylori

<400> SEQUENCE: 21

Lys Pro Lys Arg Phe Leu Val Leu Asp Leu Asn Gln Gly Tyr Arg Ile
1               5                   10                  15

Ile Leu Val Lys
            20

<210> SEQ ID NO 22
<211> LENGTH: 20
<212> TYPE: PRT
<213> ORGANISM: Helicobacter pylori
```

-continued

```
<400> SEQUENCE: 22

Gly Asn His Gly Ile Gly Phe Ala Ile Pro Ser Asn Met Val Lys Asp
1               5                   10                  15

Ile Val Thr Gln
            20

<210> SEQ ID NO 23
<211> LENGTH: 20
<212> TYPE: PRT
<213> ORGANISM: Helicobacter pylori

<400> SEQUENCE: 23

Ser Tyr Asp Asn Lys Glu Gly Ala Val Val Ile Ser Val Glu Lys Asp
1               5                   10                  15

Ser Pro Ala Lys
            20

<210> SEQ ID NO 24
<211> LENGTH: 20
<212> TYPE: PRT
<213> ORGANISM: Helicobacter pylori

<400> SEQUENCE: 24

Thr Glu Lys Lys Ile Lys Asn Asn Phe Ile Gly Gly Gly Val Phe Asn
1               5                   10                  15

Asp Pro Phe Phe
            20

<210> SEQ ID NO 25
<211> LENGTH: 20
<212> TYPE: PRT
<213> ORGANISM: Helicobacter pylori

<400> SEQUENCE: 25

Phe Ser Asp Ser Asn Asp Ile Leu Val Gly Asp Leu Val Phe Ala Ile
1               5                   10                  15

Gly Asn Pro Phe
            20

<210> SEQ ID NO 26
<211> LENGTH: 20
<212> TYPE: PRT
<213> ORGANISM: Helicobacter pylori

<400> SEQUENCE: 26

Lys Ile Lys Val Thr Ile Pro Gly Ser Asn Lys Glu Tyr Ser Ala Thr
1               5                   10                  15

Leu Val Gly Thr
            20

<210> SEQ ID NO 27
<211> LENGTH: 20
<212> TYPE: PRT
<213> ORGANISM: Helicobacter pylori

<400> SEQUENCE: 27

Ser Met Arg Leu Ser Asp Asp Val Gln Gly Val Leu Val Ser Gln Val
1               5                   10                  15

Asn Glu Asn Ser
            20
```

-continued

<210> SEQ ID NO 28
<211> LENGTH: 20
<212> TYPE: PRT
<213> ORGANISM: Helicobacter pylori

<400> SEQUENCE: 28

Ile Pro Lys Glu Arg Met Glu Arg Ala Leu Gly Ser Gly Val Ile Ile
1               5                   10                  15

Ser Lys Asp Gly
            20

<210> SEQ ID NO 29
<211> LENGTH: 20
<212> TYPE: PRT
<213> ORGANISM: Helicobacter pylori

<400> SEQUENCE: 29

Val Leu Val Ser Gln Val Asn Glu Asn Ser Pro Ala Glu Gln Ala Gly
1               5                   10                  15

Phe Arg Gln Gly
            20

<210> SEQ ID NO 30
<211> LENGTH: 20
<212> TYPE: PRT
<213> ORGANISM: Helicobacter pylori

<400> SEQUENCE: 30

Thr Asn Glu Leu Arg Asn Leu Ile Gly Ser Met Leu Pro Asn Gln Arg
1               5                   10                  15

Val Thr Leu Lys
            20

<210> SEQ ID NO 31
<211> LENGTH: 135
<212> TYPE: PRT
<213> ORGANISM: Helicobacter pylori

<400> SEQUENCE: 31

Ser Gly Val Ile Ile Ser Lys Asp Gly Tyr Ile Val Thr Asn Asn His
1               5                   10                  15

Val Ile Asp Gly Ala Asp Lys Ile Lys Val Thr Ile Pro Gly Ser Asn
                20                  25                  30

Lys Glu Tyr Ser Ala Thr Leu Val Gly Thr Asp Ser Glu Ser Asp Leu
            35                  40                  45

Ala Val Ile Arg Ile Thr Lys Asp Asn Leu Pro Thr Ile Lys Phe Ser
        50                  55                  60

Asp Ser Asn Asp Ile Leu Val Gly Asp Leu Val Phe Ala Ile Gly Asn
65                  70                  75                  80

Pro Phe Gly Val Gly Glu Ser Val Thr Gln Gly Ile Val Ser Ala Leu
                85                  90                  95

Asn Lys Ser Gly Ile Gly Ile Asn Ser Tyr Glu Asn Phe Ile Gln Thr
            100                 105                 110

Asp Ala Ser Ile Asn Pro Gly Asn Ser Gly Gly Ala Leu Ile Asp Ser
        115                 120                 125

Arg Gly Gly Leu Val Gly Ile
    130                 135

<210> SEQ ID NO 32
<211> LENGTH: 88

<212> TYPE: PRT
<213> ORGANISM: Helicobacter pylori

<400> SEQUENCE: 32

Gly Tyr Leu Gly Val Gly Leu Gln Asp Leu Ser Gly Asp Leu Gln Asn
1               5                   10                  15

Ser Tyr Asp Asn Lys Glu Gly Ala Val Val Ile Ser Val Glu Lys Asp
                20                  25                  30

Ser Pro Ala Lys Lys Ala Gly Ile Leu Val Trp Asp Leu Ile Thr Glu
            35                  40                  45

Val Asn Gly Lys Lys Val Lys Asn Thr Asn Glu Leu Arg Asn Leu Ile
        50                  55                  60

Gly Ser Met Leu Pro Asn Gln Arg Val Thr Leu Lys Val Ile Arg Asp
65                  70                  75                  80

Lys Lys Glu Arg Thr Phe Thr Leu
                85

<210> SEQ ID NO 33
<211> LENGTH: 88
<212> TYPE: PRT
<213> ORGANISM: Helicobacter pylori

<400> SEQUENCE: 33

Gly Tyr Leu Gly Val Gly Leu Gln Asp Leu Ser Gly Asp Leu Gln Asn
1               5                   10                  15

Ser Tyr Asp Asn Lys Glu Gly Ala Val Val Ile Ser Val Glu Lys Asp
                20                  25                  30

Ser Pro Ala Lys Lys Ala Gly Ile Leu Val Trp Asp Leu Ile Thr Glu
            35                  40                  45

Val Asn Gly Lys Lys Val Lys Asn Thr Asn Glu Leu Arg Asn Leu Ile
        50                  55                  60

Gly Ser Met Leu Pro Asn Gln Arg Val Thr Leu Lys Val Ile Arg Asp
65                  70                  75                  80

Lys Lys Glu Arg Ala Phe Thr Leu
                85

<210> SEQ ID NO 34
<211> LENGTH: 88
<212> TYPE: PRT
<213> ORGANISM: Helicobacter pylori

<400> SEQUENCE: 34

Gly Tyr Leu Gly Val Gly Leu Gln Asp Leu Ser Gly Asp Leu Gln Asn
1               5                   10                  15

Ser Tyr Asp Asn Lys Glu Gly Ala Val Val Ile Ser Val Glu Lys Asp
                20                  25                  30

Ser Pro Ala Lys Lys Ala Gly Ile Leu Val Trp Asp Leu Ile Thr Glu
            35                  40                  45

Val Asn Gly Lys Lys Val Lys Asn Thr Asn Glu Leu Arg Asn Leu Ile
        50                  55                  60

Gly Ser Met Leu Pro Asn Gln Arg Val Thr Leu Lys Ile Ile Arg Asp
65                  70                  75                  80

Lys Lys Glu Arg Thr Phe Thr Leu
                85

<210> SEQ ID NO 35
<211> LENGTH: 88
<212> TYPE: PRT

<213> ORGANISM: Helicobacter pylori

<400> SEQUENCE: 35

Gly Tyr Leu Gly Val Gly Leu Gln Asp Leu Ser Asp Leu Gln Asn
1               5                   10                  15

Ser Tyr Asp Asn Lys Glu Gly Ala Val Val Ile Ser Val Glu Lys Asp
            20                  25                  30

Ser Pro Ala Lys Lys Ala Gly Ile Leu Val Trp Asp Leu Ile Thr Glu
        35                  40                  45

Val Asn Gly Lys Lys Ile Lys Asn Thr Asn Glu Leu Arg Asn Leu Ile
50                  55                  60

Gly Ser Met Leu Pro Asn Gln Arg Val Thr Leu Lys Val Ile Arg Asp
65                  70                  75                  80

Lys Lys Glu Arg Thr Phe Thr Leu
                85

<210> SEQ ID NO 36
<211> LENGTH: 77
<212> TYPE: PRT
<213> ORGANISM: Helicobacter pylori

<400> SEQUENCE: 36

Gly Leu Gln Val Glu Asp Leu Thr Gln Lys Thr Lys Arg Ser Met Arg
1               5                   10                  15

Leu Ser Asp Asp Val Gln Gly Val Leu Val Ser Gln Val Asn Glu Asn
            20                  25                  30

Ser Pro Ala Glu Gln Ala Gly Phe Arg Gln Gly Asn Ile Ile Thr Lys
        35                  40                  45

Ile Glu Glu Ile Glu Val Lys Ser Val Ala Asp Phe Asn His Ala Leu
50                  55                  60

Glu Lys Tyr Lys Gly Lys Pro Lys Arg Phe Leu Val Leu
65                  70                  75

<210> SEQ ID NO 37
<211> LENGTH: 22
<212> TYPE: DNA
<213> ORGANISM: Artificial Sequence
<220> FEATURE:
<223> OTHER INFORMATION: Oligonucleotide primer

<400> SEQUENCE: 37
ggctatggat aaggatcaac gc                                      22

<210> SEQ ID NO 38
<211> LENGTH: 22
<212> TYPE: DNA
<213> ORGANISM: Artificial Sequence
<220> FEATURE:
<223> OTHER INFORMATION: Oligonucleotide primer

<400> SEQUENCE: 38
ccaccgcctt aatagagtcc tt                                      22

<210> SEQ ID NO 39
<211> LENGTH: 32
<212> TYPE: DNA
<213> ORGANISM: Artificial Sequence
<220> FEATURE:
<223> OTHER INFORMATION: Oligonucleotide primer

<400> SEQUENCE: 39

```
aaggatccgg caatatccaa atccagagca tg                          32
```

<210> SEQ ID NO 40
<211> LENGTH: 30
<212> TYPE: DNA
<213> ORGANISM: Artificial Sequence
<220> FEATURE:
<223> OTHER INFORMATION: Oligonucleotide primer

<400> SEQUENCE: 40

```
aagaattcga cccacccta tcatttcacc                              30
```